United States Patent
Arnold et al.

(10) Patent No.: US 9,039,645 B2
(45) Date of Patent: *May 26, 2015

(54) ORTHOPEDIC DEVICE PROVIDING ACCESS TO WOUND SITE

(75) Inventors: William Arnold, Woodland Hills, CA (US); Michael Campos, Sylmar, CA (US); Chad Leeder, Newbury Park, CA (US); David Armstrong, Green Oaks, IL (US)

(73) Assignee: OSSUR HF, Reykjavik (IS)

( * ) Notice: Subject to any disclaimer, the term of this patent is extended or adjusted under 35 U.S.C. 154(b) by 121 days.

This patent is subject to a terminal disclaimer.

(21) Appl. No.: 13/196,323

(22) Filed: Aug. 2, 2011

(65) Prior Publication Data

US 2011/0288461 A1    Nov. 24, 2011

Related U.S. Application Data

(63) Continuation of application No. 12/149,047, filed on Apr. 25, 2008, now Pat. No. 8,021,317.

(60) Provisional application No. 60/907,995, filed on Apr. 26, 2007, provisional application No. 60/960,782, filed on Oct. 15, 2007.

(51) Int. Cl.
*A43B 7/00* (2006.01)
*A43B 7/14* (2006.01)
(Continued)

(52) U.S. Cl.
CPC ... *A43B 7/00* (2013.01); *A43B 7/14* (2013.01); *A43B 7/147* (2013.01); *A43B 7/22* (2013.01);
(Continued)

(58) Field of Classification Search
CPC ..... A61F 5/0111; A61F 5/0127; A61F 13/04; A61F 5/0193; A61F 5/019; A61F 13/066; A61F 5/0585; A43B 7/20
USPC .......... 602/5, 12, 16, 23, 27, 28, 29; 128/882; 36/88, 140, 155
See application file for complete search history.

(56) References Cited

U.S. PATENT DOCUMENTS 2,491,280 A    12/1949   Roth
4,057,056 A *  11/1977   Payton ........................... 602/11
(Continued)

FOREIGN PATENT DOCUMENTS

DE    90 00 405 U1    3/1990
EP    1 504 736        2/2005
(Continued)

OTHER PUBLICATIONS

Piaggesi et al., "An Off-the-Shelf Instant Contact Casting Device for the Management of Diabetic Foot Ulcers", Diabetes Care, vol. 30, No. 3, Mar. 2007.

(Continued)

*Primary Examiner* — Alireza Nia
*Assistant Examiner* — Ophelia A Hawthorne
(74) *Attorney, Agent, or Firm* — Workman Nydegger

(57) ABSTRACT

Orthopedic device for treating neuropathic ulcers and other injuries while allowing easy access to the wound site on the plantar surface of a patient's foot includes a base portion and a sole that is either movably connected or removably connected to either the base or to a strut member. The base or strut is maintained in position on the lower leg while the sole may be rotated, slid, or completely removed for allowing inspection and access to the plantar surface of the patient's foot.

15 Claims, 17 Drawing Sheets

(51) Int. Cl.
*A43B 7/22* (2006.01)
*A43B 11/00* (2006.01)
*A43B 13/14* (2006.01)
*A61F 5/01* (2006.01)

(52) U.S. Cl.
CPC ............... *A43B 11/00* (2013.01); *A43B 13/145* (2013.01); *A61F 5/0102* (2013.01); *A61F 5/0127* (2013.01); *A61F 5/0195* (2013.01)

(56) References Cited

U.S. PATENT DOCUMENTS

| | | | |
|---|---|---|---|
| 4,155,179 A * | 5/1979 | Weninger | 36/117.4 |
| 4,962,760 A * | 10/1990 | Jones | 602/27 |
| 5,250,012 A * | 10/1993 | Meredith | 482/54 |
| 5,250,021 A | 10/1993 | Chang | |
| 5,368,551 A * | 11/1994 | Zuckerman | 602/23 |
| 5,370,133 A | 12/1994 | Darby et al. | |
| 5,370,604 A | 12/1994 | Bernardoni | |
| 5,399,149 A | 3/1995 | Frankowiak | |
| 5,426,872 A * | 6/1995 | Hayes | 36/118.9 |
| 5,445,603 A | 8/1995 | Wilkerson | |
| 5,571,077 A | 11/1996 | Klearman et al. | |
| 5,609,570 A | 3/1997 | Lamont | |
| 5,665,059 A | 9/1997 | Klearman et al. | |
| 5,761,834 A | 6/1998 | Grim et al. | |
| 5,865,778 A | 2/1999 | Johnson | |
| 5,913,841 A * | 6/1999 | Lamont | 602/65 |
| 6,056,712 A | 5/2000 | Grim | |
| 6,155,998 A | 12/2000 | Gilmour | |
| 6,228,044 B1 | 5/2001 | Jensen et al. | |
| 6,277,087 B1 * | 8/2001 | Hess et al. | 602/27 |
| 6,610,897 B2 | 8/2003 | Cavanagh et al. | |
| 6,648,843 B1 * | 11/2003 | Marciano et al. | 602/27 |
| 6,682,497 B2 | 1/2004 | Jensen et al. | |
| 6,720,470 B2 | 4/2004 | Cavanagh et al. | |
| 6,945,946 B2 | 9/2005 | Rooney | |
| 7,294,114 B1 | 11/2007 | Clement et al. | |
| 7,384,584 B2 * | 6/2008 | Jerome et al. | 264/222 |
| 7,563,238 B1 * | 7/2009 | Breashears | 602/27 |
| 8,454,546 B2 * | 6/2013 | Campos et al. | 602/27 |
| 2001/0051780 A1 * | 12/2001 | Birmingham | 602/27 |
| 2002/0029009 A1 | 3/2002 | Bowman | |
| 2002/0095105 A1 | 7/2002 | Jensen | |
| 2002/0128574 A1 | 9/2002 | Darby | |
| 2002/0138030 A1 | 9/2002 | Cavanagh et al. | |
| 2003/0196352 A1 | 10/2003 | Bledsoe et al. | |
| 2003/0199798 A1 | 10/2003 | Gilmour | |
| 2003/0212358 A1 | 11/2003 | Cavanagh et al. | |
| 2003/0216675 A1 | 11/2003 | Rooney | |
| 2004/0103561 A1 | 6/2004 | Campbell et al. | |
| 2004/0111048 A1 | 6/2004 | Jensen et al. | |
| 2004/0168354 A1 | 9/2004 | Nguyen | |
| 2005/0172517 A1 | 8/2005 | Bledsoe et al. | |
| 2005/0240133 A1 | 10/2005 | Rooney | |
| 2009/0133292 A1 | 5/2009 | Salvatelli et al. | |

FOREIGN PATENT DOCUMENTS

| | | |
|---|---|---|
| EP | 1 593 360 A2 | 11/2005 |
| WO | 2008/021986 A2 | 2/2008 |
| WO | WO 2008/113321 | 9/2008 |

OTHER PUBLICATIONS

M. Myerson, the Total-contact Cast for Management of Neuropathic Planter Ulceration of the Foot, pp. 261-269. Mar. 20, 2007.
Casting, Bureau of Primary Health Care, NHDP, Retrieved Nov. 20, 2007 <http:/ /bphc.hrsa.govinhdp/CASTING_PT>.
Total Contact Cast: What It Is and Why It's Used. American Academy of Family Physicians. Nov. 2006.
Calzature taglie forth e ortopediche Optima-Molliter. Retrieved Sep. 27, 2007 <http:/ /www.molliter.com/index.php?intel=eng>.
IPRO 309 Orthotics and Prosthetics Education in Latin America, Retrieved Sep. 27, 2007.<http:/ /www.iit.edu/~ipro309sO7>.
Supplementary European Search Report issued in PCT/US2008/005326, Oct. 20, 2011.

* cited by examiner

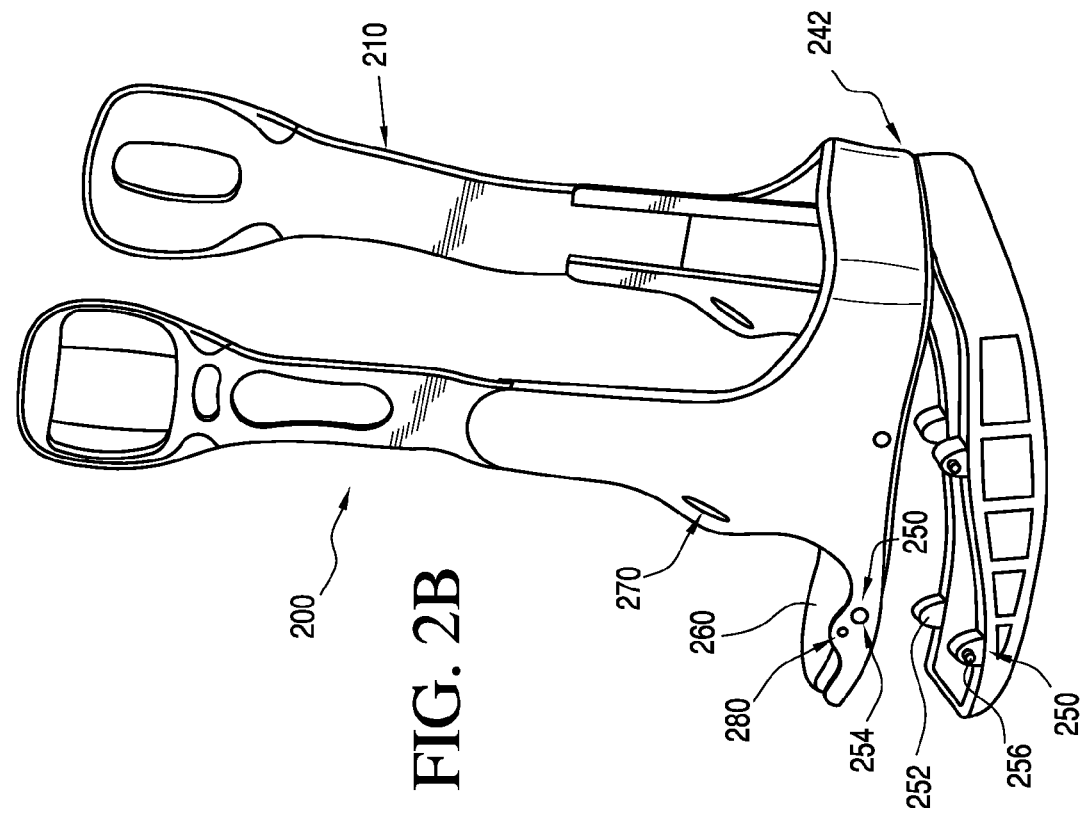
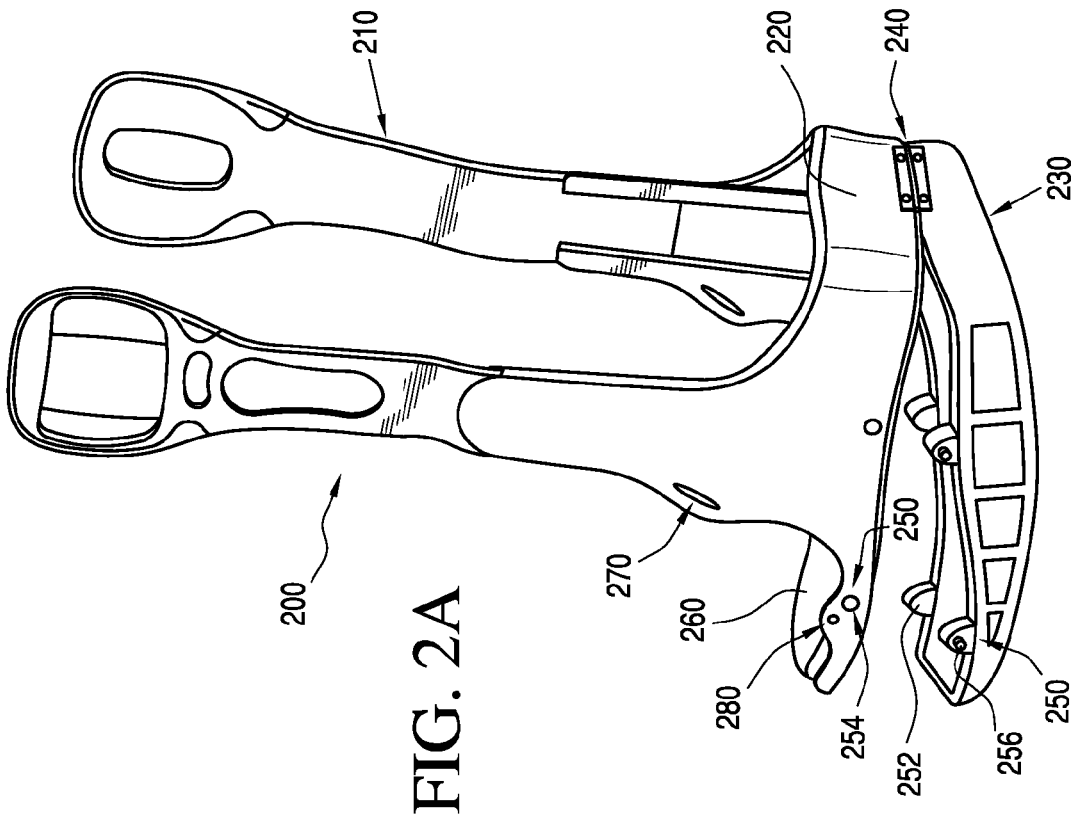

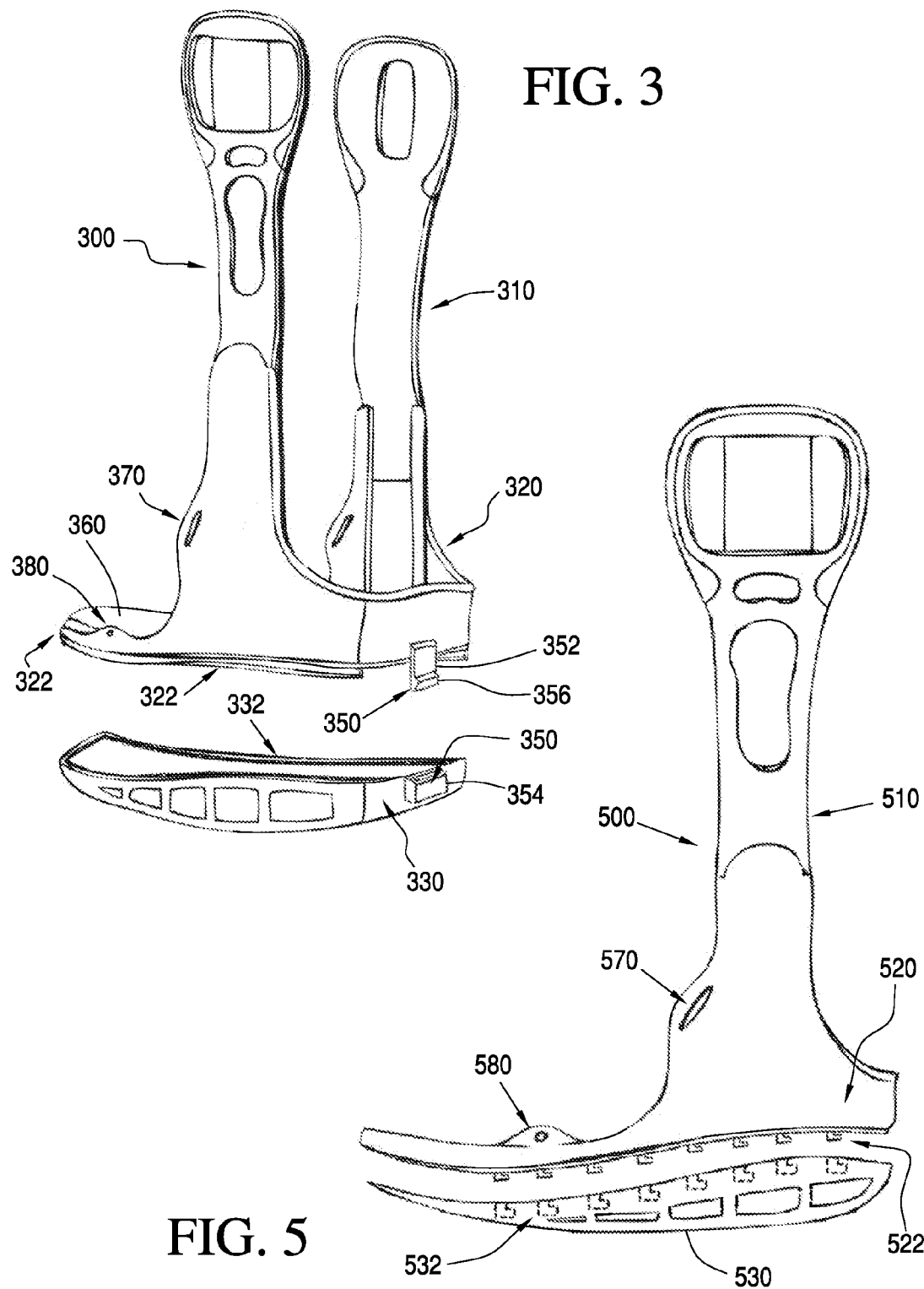

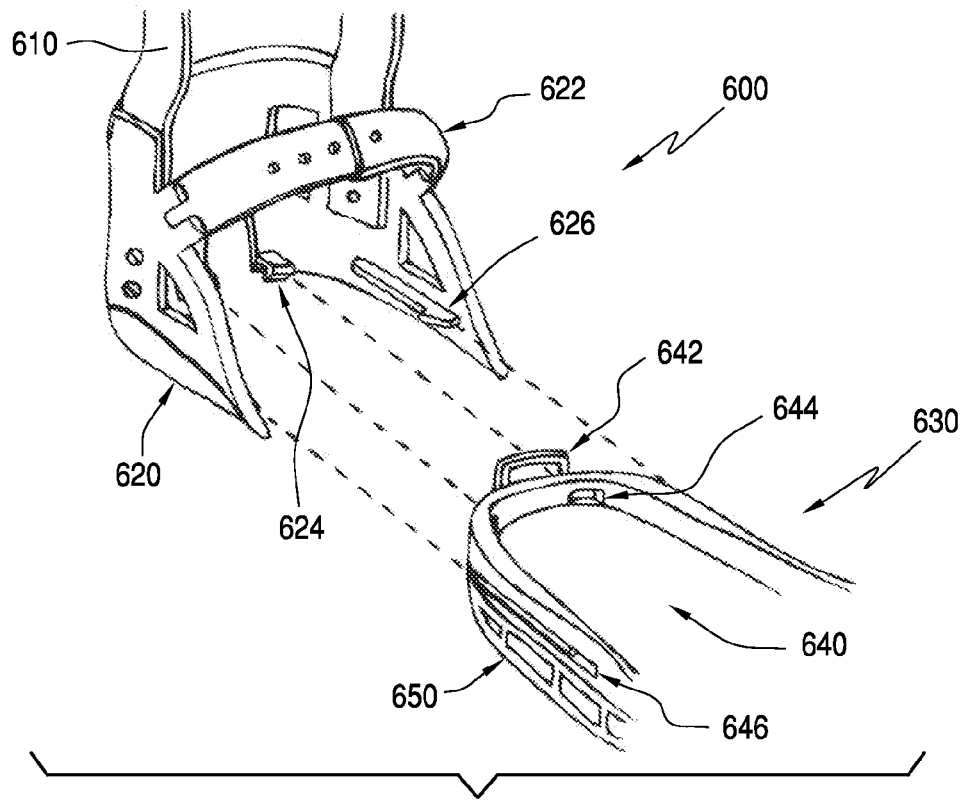
FIG. 6
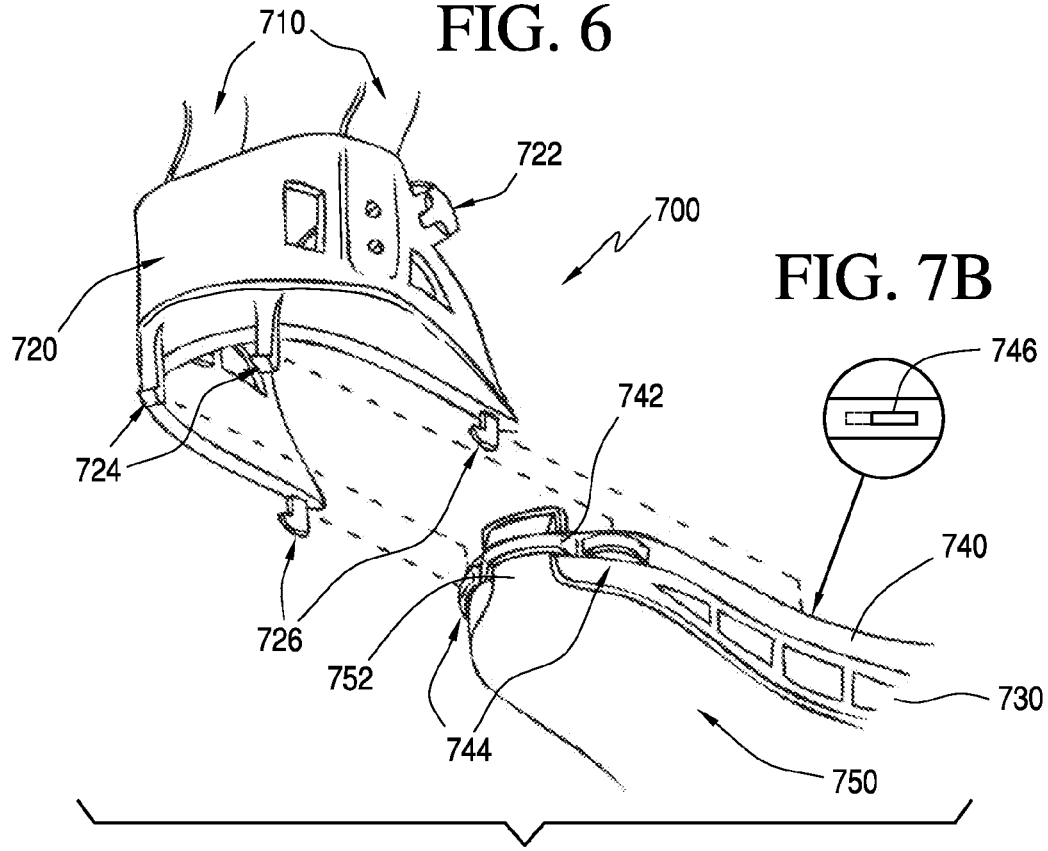
FIG. 7B
FIG. 7A

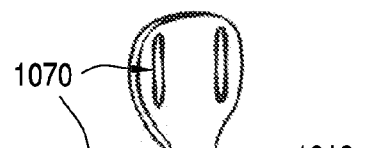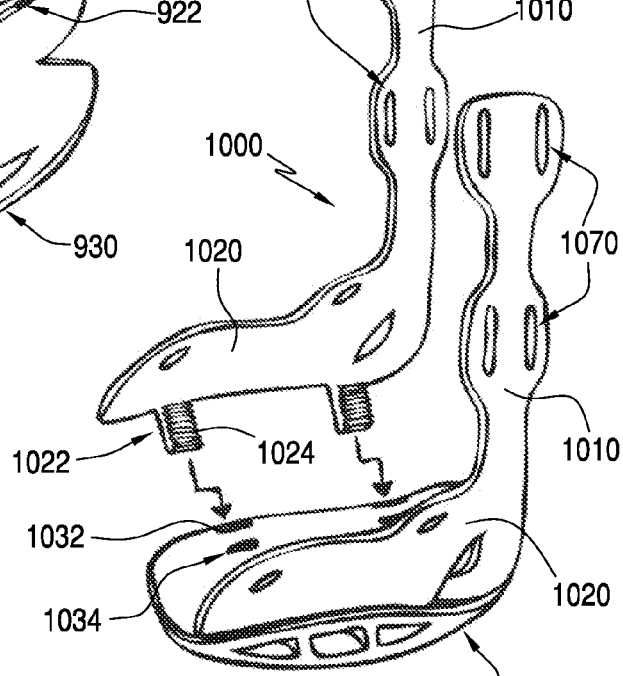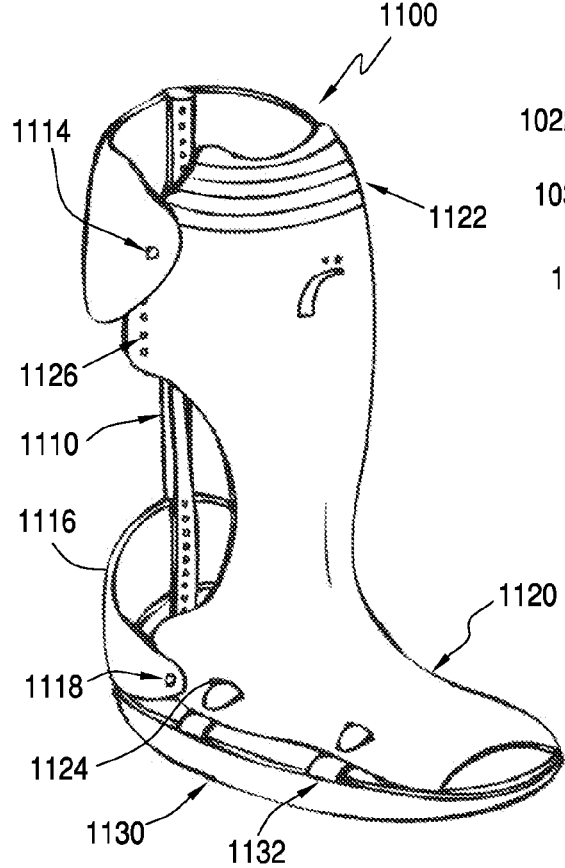
FIG. 9
FIG. 10
FIG. 11

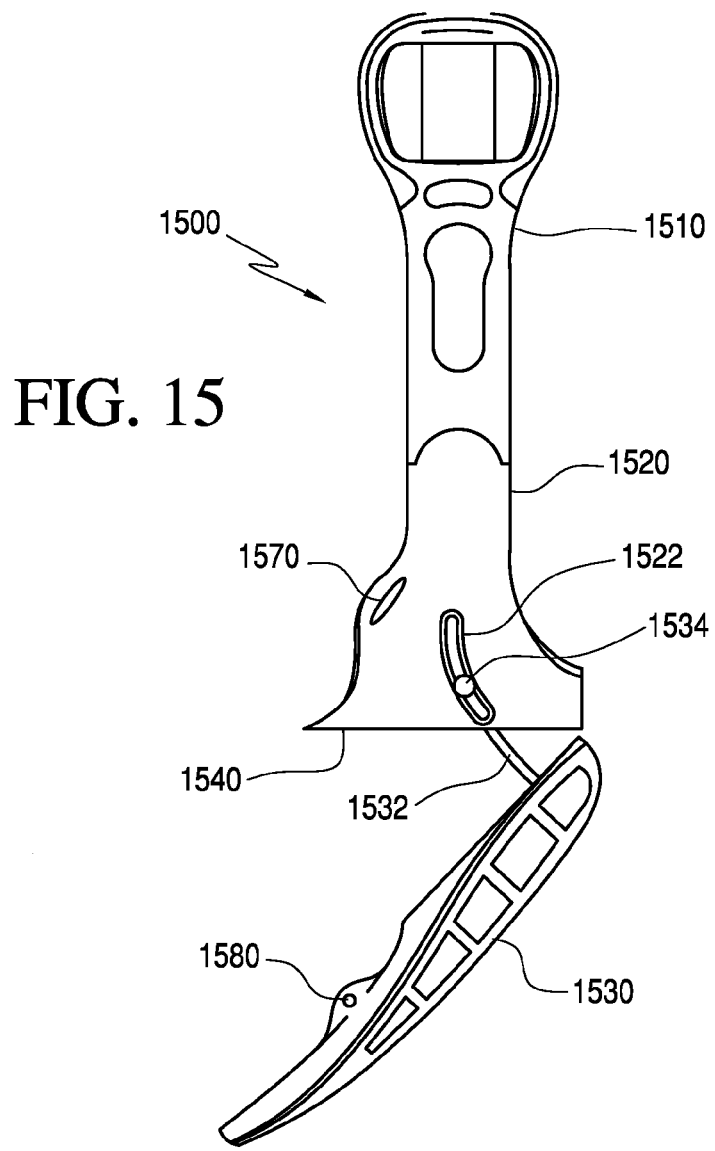

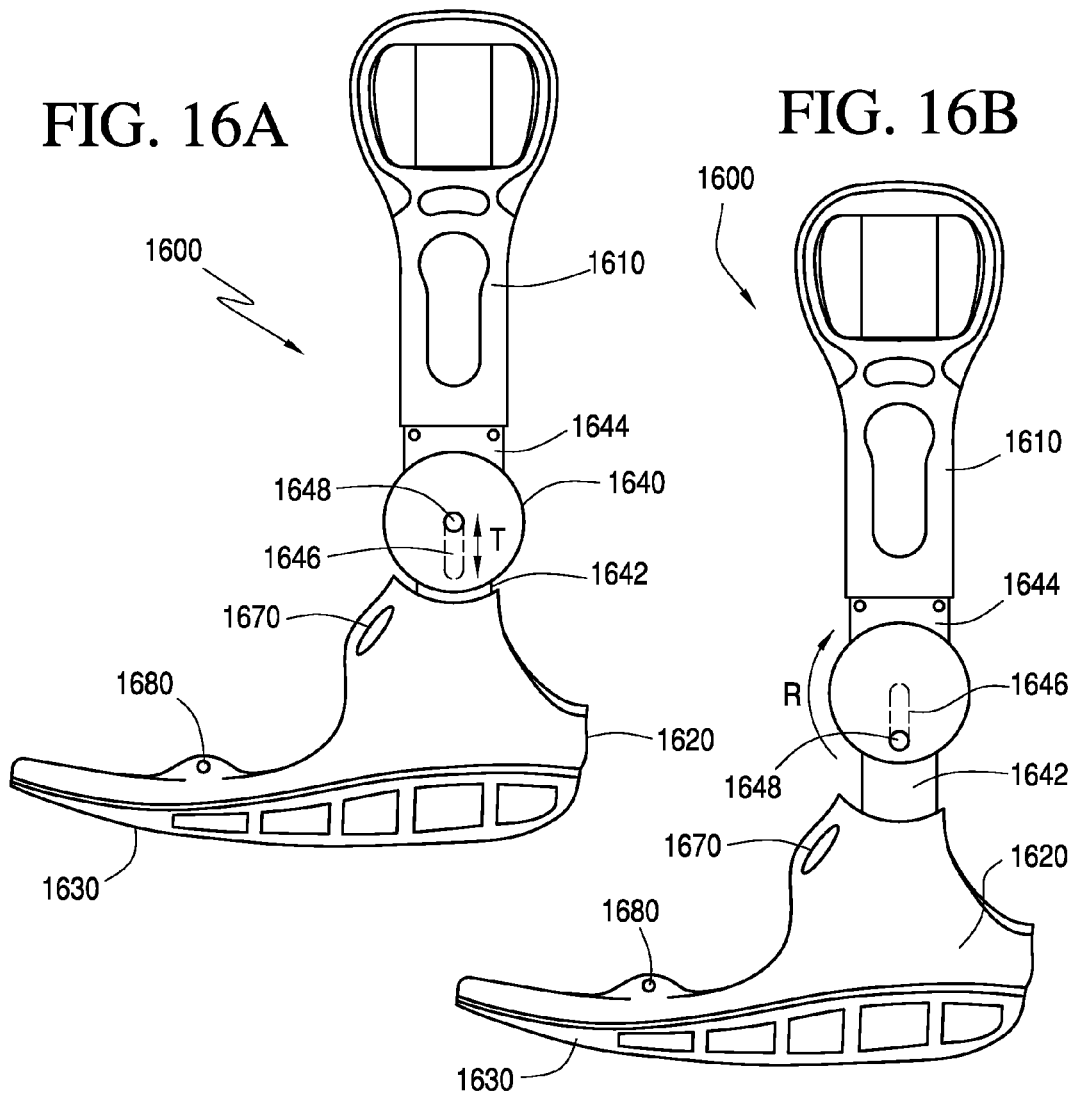
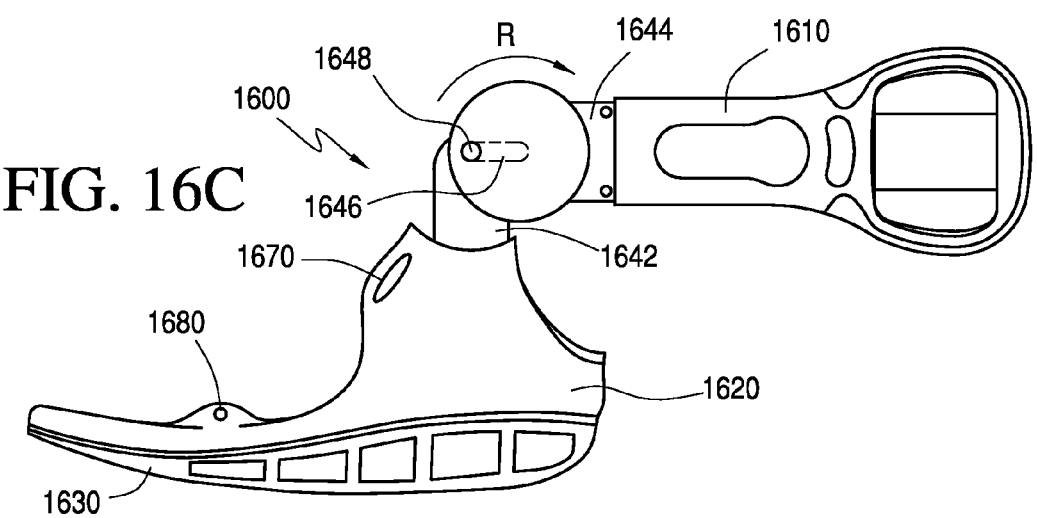

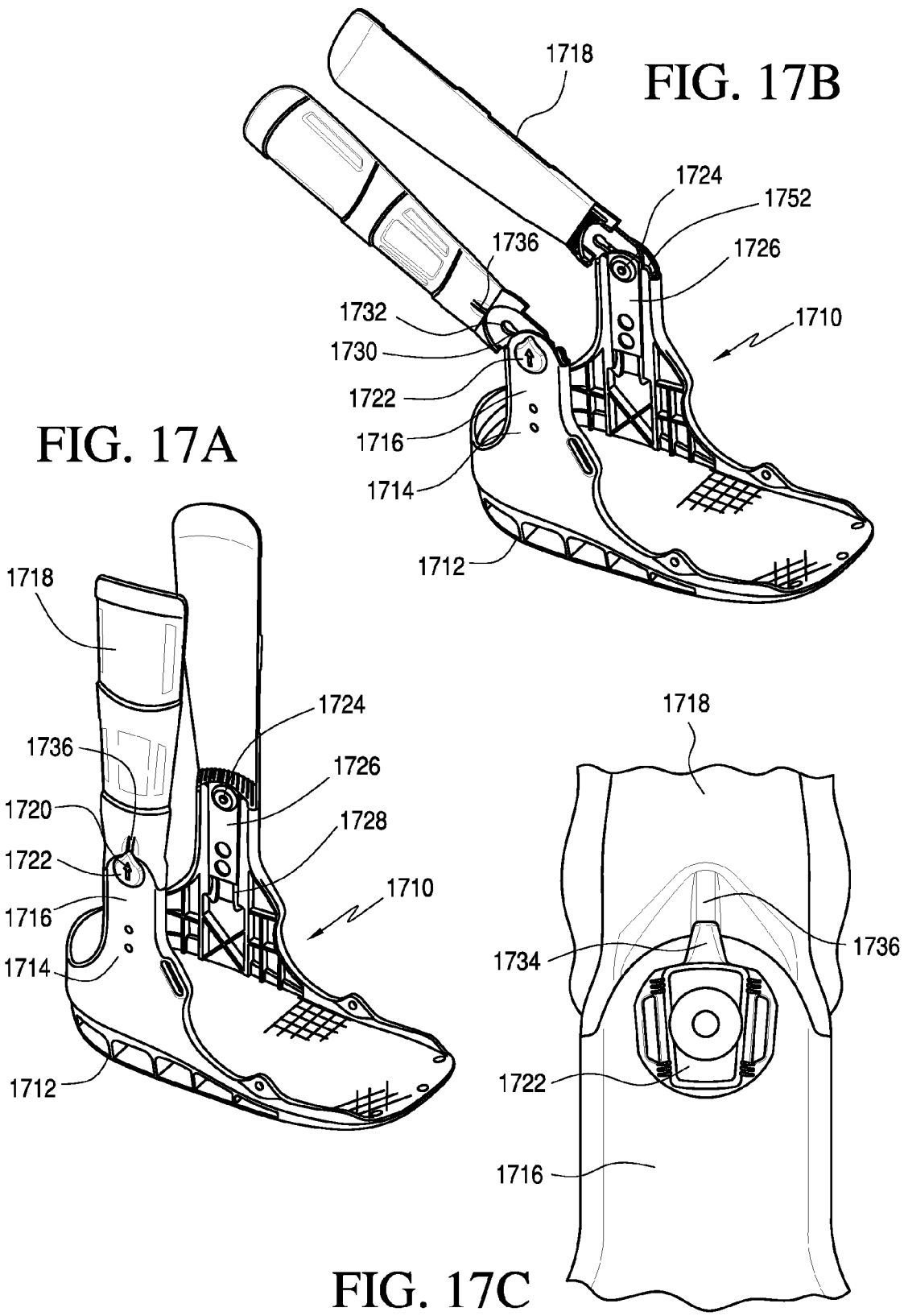

ORTHOPEDIC DEVICE PROVIDING ACCESS TO WOUND SITE

CROSS-REFERENCE TO RELATED APPLICATIONS

This application is a continuation of U.S. application Ser. No. 12/149,047, filed on Apr. 25, 2008, which claims the benefit of priority from U.S. provisional application No. 60/907,995, filed on Apr. 26, 2007, and U.S. provisional application No. 60/960,782, filed on Oct. 15, 2007.

FIELD OF THE INVENTION

The present invention relates generally to the field of orthopedic or prosthetic devices and more particularly to an orthopedic or prosthetic device allowing easy access to a wound site including tissues adjacent to or covered by the orthopedic or prosthetic device.

BACKGROUND

Foot ulcers represent one of the most notable risk factors for lower extremity amputations in persons diagnosed with diabetes mellitus, a disorder in which blood sugar (glucose) levels are abnormally high because the body does not produce enough insulin. Persons diagnosed with diabetes are typically classified as slow healers and are prone to debilitating foot ulcers due to both neurological and vascular complications. Peripheral neuropathy, or a deadening of the nerves, can cause altered or complete loss of tactile sensation in the foot and/or leg, and in this regard, the diabetic patient with advanced neuropathy tends to loose the ability to discriminate between sharp-dull tactile sensations. Accordingly, any cuts or trauma to the foot of a diabetic patient with advanced neuropathy often go unnoticed for lengthy periods of time, and may develop into neuropathic ulcers.

Further, a deformity commonly known as "charcot foot" occurs as a result of decreased sensation. Patients with "normal" tactile sensation in their feet automatically determine when too much pressure is being placed on an area of the foot. Once identified, the human body instinctively shifts position to relieve the stress. A patient with advanced neuropathy looses this important mechanism. As a result, tissue ischemia and necrosis, or a restriction in blood supply or a deadening of the tissue, may occur and thus lead to plantar ulcers. Microfractures in the bones of the foot thus may go unnoticed and untreated, resulting in disfigurement, chronic swelling and additional bony prominences.

Microvascular disease is an additional problem for diabetic patients, which can also lead to foot ulcers. It is well known that diabetes often results in a narrowing of smaller arteries, which narrowing cannot be resolved surgically. This microvascularization thus further prompts the diabetic patient to adhere to a strict glucose level regimen, maintain an ideal body weight and cease tobacco smoking in an attempt to reduce the onset of microvascular disease.

Should a diabetic patient develop a plantar ulcer, for whatever reason, treatment options are generally limited to a twofold treatment plan. In the first instance, the prime objective is to obtain wound closure, which eliminates a portal of entry for bacterial invasion and development of limb-threatening infection. In the second instance, a further objective is to allow for a reduction in pressures on the foot or the "offloading" of tissues. In this regard, protective orthopedic footwear has been shown to lower sited foot pressures and further has been shown to contribute to the healing and closing of wounds. Moreover, once a given plantar ulcer has been effectively closed, protective orthopedic footwear has been shown to prevent the reoccurrence of plantar ulcers.

A number of factors guide the selection of the appropriate off-loading modality for a particular patient. A few of these factors are patient compliance, comfort, ease of application, and cost. Common methods of off-loading plantar ulcers are the use of total contact casts or lower leg walking boots.

Lower leg walking boots, also known as removable cast walkers, are often chosen in order to reduce application time and to allow the physician to have easy access to the wound site for wound care procedures. Exemplary walkers are disclosed in U.S. Pat. No. 5,078,128, granted January 1992, U.S. Pat. No. 5,329,705, granted July. 1994, and U.S. Pat. No. 5,378,223, granted Jan. 3, 1995, and in U.S. publication no. 2004/0019307, all assigned to Royce Medical Co. and all incorporated herein by reference. Walkers are usually quite easy to apply and remove, typically utilizing straps with VELCRO (hook and loop fasteners) or buckles.

However, the same ease with which a physician may remove the walker in order to inspect and treat the wound site also allows patients to remove the walker outside of the presence of the physician. Thus one concern with the use of walkers is that the healing of the ulcer will be severely compromised by patients removing the walker and ambulating without the product applied. A physician is thus left to wonder with each application of a walking boot whether the patient will follow the advice of the clinician or whether the healing will be compromised by the patient removing the walker. Studies done by members of this research team and others have suggested that patients with plantar wounds secondary to diabetes only wear their off-loading device for an average of 28 percent of their daily activity.

In comparison, the total contact cast (TCC) has generally been considered the gold standard for off-loading plantar ulcers. The concept of utilizing the total contact cast to treat plantar ulcers was developed in the 1950's. The total contact cast must be applied and removed by a physician or a practitioner in a number of steps, as will be understood by the skilled artisan. The application is time consuming, since an inner shell of plaster must by applied and allowed to fully dry, and then an exterior shell of plaster must be applied.

The exterior shell must typically be allowed to dry for a full 24 hours before a patient can put any weight on the TCC. Additionally, the TCC must be removed at least once every one to two weeks, if not more frequently, so that the physician can inspect and treat the plantar ulcerations. Of course, removal of the TCC requires another application of a TCC. Thus, it seems that the use of walkers is a more efficient and economic manner of treating plantar ulcerations.

Thus, there is a need for a device that allows easy access to wounds on the plantar surface of the foot without removal and reapplication of the entire device. Accordingly, diabetic footwear allowing easy access to wounds on the plantar surface of a patient's foot is provided that solves these and other problems associated with previous designs.

SUMMARY

As discussed above, current orthopedic products require a clinician to remove the entire apparatus from the patient in order to inspect and treat wounds on the plantar surface of the patient's foot. While these devices provide improved patient compliance, they are also relatively expensive and time consuming to apply. Further, due to the requirement that the wounds be checked weekly, or sometimes daily, the repeated removal and application or reapplication of an orthopedic device also adds to the costs.

Accordingly, an orthopedic device or orthopedic footwear in the form of an off-loading walkers or low top boots, generally referred herein as "diabetic walker," with removable or detachable bases and/or sole areas that allow the inspection and treatment of the plantar surface of the foot are proposed. There are two main components of the diabetic walker: the base/sole and strut. The base/sole component is the area that surrounds and supports the foot when the walker is in use. The strut component involves the strapping system or any apparatus used to secure the leg to the strut(s) to immobilize the leg.

In order to allow a clinician easy access to the plantar surface of the foot, the diabetic walker has a movable or a removable/detachable base and/or sole area that allows the practitioner access to the plantar surface of the foot without requiring removal of the strut component from the patient's leg. In other words the strut component remains on the patient's leg when the base/sole area is removed. Thus, the clinician is not required to completely remove and replace or to remove and reapply the orthopedic device. Accordingly, the time required for each patient visit can be greatly reduced, as well as reducing the costs associated with the treatment.

In further details of disclosed embodiments, there may be locking mechanisms to hold the base/sole area to the strut area when the off-loading walker is in use. A release mechanism may be incorporated with or may be separate from the locking mechanism in order to aid with removal or detachment of the two areas. Appropriate locking mechanisms may be provided on both the walker and the sole assemblies so that the patient may not remove either without a practitioner or physician present.

Exemplary embodiments may include an off-loading walking boot that has a sole or bottom portion that hingedly detaches or swivels away from the plantar aspect of the foot to allow visual inspection and dressing changes. Alternatively, an off-loading walking boot may include a sole or bottom portion with a sliding window section for viewing and treating the plantar surface of the foot. In yet another alternative, a pattern of fiberglass composite material may be formed into the shape of a lower leg cast that contains a removable section for visualizing the plantar surface of the foot.

A number of embodiments of orthopedic devices in the form of orthopedic devices, diabetic walkers and footwear with easy access to a wound site are disclosed herein to provide an improved orthopedic device that alleviates or eliminates the above described and other shortcomings of the previous orthopedic devices for treating plantar ulcerations and other foot injuries. These embodiments include improvements in the structure and use of diabetic footwear in the form of an off-loading walking boot that allows the physician or practitioner to have access to the plantar surface of the patient's foot without having to completely remove the orthopedic device. Further, the structures may include retaining mechanisms that prevent unauthorized removal of the device or unauthorized access to the plantar surface of the foot.

In accordance with one embodiment of the invention, an orthopedic device includes at least one strut member extending from a base portion. The strut member is secured to the patient's limb utilizing appropriate mechanisms, such as straps having hook and loop fasteners. Additional structure, such as a retaining strap, may be provided in order to prevent the unauthorized removal of the orthopedic device.

A sole portion is provided along a distal portion of the base portion for providing the walking surface of the orthopedic device. An insole or cushion is positioned along the sole portion and the base portion and to define the contact surface for contacting the plantar aspect of a foot. Alternatively, the insole or cushion may be integral with or defined by the sole portion. The sole portion is movable with respect to the base portion in order to allow access to the plantar aspect of the foot.

In a variation, the sole portion is attached to the base portion at a rotatable connection, such as a swivel rivet, a swing hinge, or a living hinge. In a further variation, a guide slot is provided in the base portion that engages a guide pin that is connected to the sole portion in order to provide a smooth opening between the sole and base portions.

In a variation, the rotatable connection between the base and the sole is positioned in a posterior portion of the sole portion and a posterior portion of the base portion in order to allow the sole portion to swing or rotate away from the base portion.

In another embodiment, a locking mechanism is provided for allowing selective movement of the sole portion and maintaining the sole portion in position during use. The locking mechanism includes a first portion positioned in a posterior portion of the sole portion. The locking mechanism also includes a second portion correspondingly positioned in a posterior portion of the base portion. The first and second portions are engageable and disengageable, wherein the locking mechanism prevents movement of the sole portion when the first and second portions are engaged.

As an alternative, the locking mechanism has a first portion positioned in an anterior portion of the sole portion and a second portion correspondingly positioned in an anterior portion of the base portion. The first and second portions are engageable and disengageable, wherein the locking mechanism prevents movement of the sole portion when the first and second portions are engaged.

In a variation, a slidable latch member is provided on a posterior portion of the base portion and a corresponding housing member for receiving the latch member is provided on a posterior portion of the sole portion.

In a further variation of the invention, at least one first locking mechanism has a first portion positioned along a lateral side of the sole portion and a second portion correspondingly positioned along a lateral side of the base portion. At least one second locking mechanism has a first portion positioned along a medial side of the sole portion and a second portion correspondingly positioned along a medial side of the base portion. The respective first and second portions are engageable and disengageable, wherein the locking mechanisms prevent movement of the sole portion when the first and second portions are engaged.

In a further variation of the movable sole, the sole portion is removably connected to the base portion in order to allow removal of the sole portion without causing any damage to the plantar surface of the foot. In this variation, a latch member is provided on a posterior portion of the base portion and a corresponding housing member is provided on a posterior portion of the sole portion for receiving the latch member. At least one slide member is provided along anterior, lateral and/or medial edges of the distal portion of the base portion. The slide member removably engages at least one corresponding guide channel provided along anterior, lateral and/or medial edges of a proximal portion of the sole portion in order to allow the sole portion to be slidably removable from the base portion.

In an alternative construction, at least one slide member is provided along anterior, lateral and/or medial edges of the distal portion of the base portion. The slide member removably engages at least one corresponding guide channel provided along anterior, lateral and/or medial edges of a proximal portion of the sole portion. This variation provides increased contact area between the connections of the sole and base portions in order to provide an improved fit.

In a variation, the base portion has a stop member positioned on an anterior portion of the distal portion of the base portion in order to retain the sole member in a predefined position on the base portion. Alternatively, a cut-out portion is provided in the base portion that is complementary shaped to a raised portion of a proximal surface of the sole portion.

In an alternate configuration of the removable sole, at least one clip member is provided along lateral and/or medial edges of the distal portion of the base portion. The clip member removably engages at least one corresponding recess provided along lateral and/or medial edges of a proximal portion of the sole portion. The at least one clip member extends distally from the distal portion of the base portion and has an anterior or posterior extending portion received in a respective anterior or posterior extending portion of the corresponding recess. Thus, the plantar surface of the foot may be accessed while the orthopedic device is retained on the user's limb.

In another configuration, the base portion includes at least one posterior lock member along the distal portion of the base portion and at least one slide lock member along a lateral or medial side of the base portion. The posterior lock member removably engages a slot portion along a posterior portion of the sole portion and the slide lock member removably engages a slot portion along a lateral or medial side of the sole portion in order to allow selective removal of the sole portion from the base portion.

In another embodiment of the present invention, an orthopedic device has at least one strut member removably connected to and extending from a base portion. A sole portion is positioned along a distal portion of the base portion. An insole or cushion member is positioned along or defined by the sole portion and is positioned along the base portion and defines the contact surface for contacting the plantar aspect of a foot. The sole portion and the base portion are movable with respect to the strut member for providing access to the plantar aspect of a foot. A locking mechanism has a first portion positioned on a proximal portion of the base portion and a second portion positioned on a distal portion of the strut member. The first portion of the locking mechanism is a raised portion and the second portion of the locking mechanism is a recessed portion. Alternatively, the first portion of the locking mechanism may be at least one recess and the second portion of the locking mechanism may be at least one projection.

In a variation, the orthopedic device includes opposed lateral and medial strut members extending from opposed lateral and medial base portions. A sole portion is positioned along a distal portion of each base portion. An insole or cushion member is defined by the sole portion or positioned along the sole and base portions and defines a contact surface for contacting the plantar aspect of a foot. The sole portion is selectively removable from the lateral and medial base portion for providing access to the plantar aspect of a foot. At least one extension member extends from each of the distal portions of the lateral and medial base portions and is received within a recess formed along respective lateral and medial sides of the sole portion. Each extension member has a ratchet surface and selectively engages a ratchet mechanism within the respective recess. This configuration allows the sole to be easily removed from the base portions and struts, thus allowing access to the plantar surface of the foot without removing the device form the patient's limb.

In another variation, the orthopedic device includes an anterior shell and at least one posterior shell having at least one locking mechanism with a first portion carried by the anterior shell and a second portion carried by the posterior shell. A sole portion is positioned along a distal portion of the anterior shell. An insole or cushion member is positioned along the sole and defines the contact surface for contacting the plantar aspect of a foot. The sole portion is selectively removable from the anterior shell for providing access to the plantar aspect of a foot. At least one strut member extends between a proximal and a distal posterior shell. The height of the strut member and the proximal and distal posterior shells is adjustable in order to provide a proper fit for user's of different sizes.

In an alternate embodiment of the inventions, an orthopedic device includes a support for the lower leg that is open at a distal end thereof. A retaining member is provided along the distal end of the support and defines an opening between anterior, lateral, posterior, and medial sides of the retaining member. A removable sole member having a projecting portion selectively engaging a lip portion is provided within the opening. A locking mechanism has a first portion positioned on the sole member and a second portion positioned on the retaining member. Thus, the plantar surface of the foot may be accessed by simple removal of the sole portion, while the support remains on the patient's limb.

In a variation, the orthopedic device includes a support for the lower leg that is open at a distal end thereof. A retaining member is received within and occluding the open distal end of the support and has at least one tab protruding from a distal surface thereof. A removable sole member has at least one passage corresponding to the protruding tab. At least one locking peg passes through the corresponding passage and selectively engages the corresponding protruding tab. The protruding tab includes a flared end selectively engaging a corresponding locking protrusion on the locking peg in order to retain the sole portion in position when in use.

In an alternate construction, the orthopedic device includes a support body defining a clip member slot on a distal surface thereof. A removable sole member has a clip member selectively engaged with the clip slot.

In a further variation of a rotatable or pivotable sole, an orthopedic device has at least one strut member secured to at least one base portion through a pivotable hinge. The orthopedic device also has a sole portion attached to or integrally formed with the base portion. Thus, the sole portion is pivotable with the base away from the plantar surface of the foot in a manner that allows a physician to inspect and treat the plantar surface of the foot, as well as a portion of the ankle Numerous variations of a retaining strap are disclosed. The variations of the retaining strap may be utilized with any of the variations or embodiments of the diabetic footwear described herein. The retaining straps provide varying degrees of restricted access or removal of the orthopedic device depending upon the level of patient compliance that a physician expects from a particular patient.

The numerous advantages, features and functions of the various embodiments of an orthopedic device with easy access to a wound site will become readily apparent and better understood in view of the following description and accompanying drawings. The following description is not intended to limit the scope of the orthopedic device with easy access to a wound site, but instead merely provides exemplary embodiments for ease of understanding.

BRIEF DESCRIPTION OF THE DRAWINGS

FIG. 2A is a side perspective view of another embodiment of an orthopedic device with easy access to a wound site.

FIG. 2B is a side perspective view of another embodiment of an orthopedic device with easy access to a wound site.

FIG. 3 is a side perspective view of another embodiment of an orthopedic device with easy access to a wound site.

FIG. 5 is a side view of another embodiment of an orthopedic device with easy access to a wound site.

FIG. 6 is a partial exploded perspective view of another embodiment of an orthopedic device.

FIG. 7A is a partial exploded perspective view of another embodiment of an orthopedic device with easy access to a wound site.

FIG. 7B is a partial inset view of a proximal surface of a lateral or medial side of the sole and slot of the embodiment of FIG. 7A.

FIG. 9 is a perspective view of another embodiment of an orthopedic device.

FIG. 10 is a perspective view of another embodiment of an orthopedic device.

FIG. 11 is a perspective view of another embodiment of an orthopedic device.

FIG. 15 is a side view of an alternate configuration for an orthopedic device.

FIG. 16 is a side view of an alternate configuration for an orthopedic device.

FIGS. 16A-C are side views of a variation of the orthopedic device of FIG. 16.

FIG. 17A is a perspective view showing another embodiment of an orthopedic device in an upright position.

FIG. 17B is a perspective view of the orthopedic device of FIG. 17A in an unlocked, hinged position.

FIG. 17C is detailed view of the lock device of FIG. 17A.

Figure 1B:
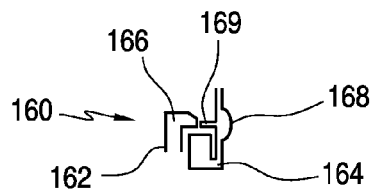
FIG. 1B is a partial view of an exemplary locking mechanism for use with an orthopedic device with easy access to a wound site.

In the various figures, similar elements are provided with similar reference numbers. It should be noted that the drawing figures are not necessarily drawn to scale, but instead are drawn to provide a better understanding of the components thereof, and are not intended to be limiting in scope, but rather provide exemplary illustrations.

DETAILED DESCRIPTION OF VARIOUS EMBODIMENTS

A. Environment and Context of the Various Embodiments

It has been found that the Total Contact Cast (TCC) heals patients more effectively than removable cast walkers. These findings, coupled with findings regarding the lack of patient compliance wile using removable cast walkers would suggest that the TCC's effectiveness lies chiefly in its ability to ensure patient compliance.

One compromise technique is the use of the Instant Total Contact Cast (ITCC), wherein a removable walker may be locked onto the patient's lower limb, such that the patient may not remove the walker. One method of achieving the ITCC is to wrap casting tape circumferentially around the walker, thereby fully enclosing the walker so that a patient cannot remove it.

While studies conducted by this group and others suggest that this technique is more effective than the use of removable cast walkers alone and as effective as the use of a TCC, there are still a number of areas where improvement is desirable.

Compliant patients are trusted with a removable off-loading walker, but are instructed to keep the walker on at all times and with removal performed only by a clinician. Each treatment requires weekly inspection visits that involve removal of the walker, debriding of the ulcer, redressing of the ulcer, and re-application of the treatment device. The off-loading walker inspection visit can be lengthy, depending on the ulcer and patient compliance, but there has been a growing demand to have a faster and easier way to access the plantar ulcer without removing the entire off-loading walker.

Clinicians are constantly removing and reapplying off-loading walkers which can become burdensome and very time consuming if numerous patients are inspected daily. Positioning of the foot and leg into the off-loading walker also becomes an issue because there is no guarantee that when the off-loading walker is reapplied the original positioning of the foot is achieved.

Additionally, once a walking boot is secured to the patient's lower limb in this manner it is not easy to inspect the wound site. As with the TCC, the patients will often undergo daily to weekly wound site checks. Each check of course requires the removal of the casting tape and the walker and the subsequent reapplication of the walker and the casting tape. Certainly if the patient is receiving this many checks the ITCC with casting tape will require several resource and time consuming applications.

Further, the method of applying casting tape or other materials around a walker is not ideal due to technique requirements, concerns about swelling of the limb, potential for pressure points from the wrapped material, etc.

Accordingly, embodiments and variations of diabetic footwear allowing easy access to a wound site on the plantar surface of the foot are described below.

For further ease of understanding the orthopedic device, orthopedic footwear or diabetic walker as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid" and "flexible" may be used herein to distinguish characteristics of portions of certain features of the orthopedic device. The term "rigid" is intended to denote that an element of the support is generally devoid of flexibility. Within the context of support members that are "rigid," it is intended to indicate that they may break if bent with sufficient force. On the other hand, the term "flexible" is intended to denote that features are capable of repeated bending. The term "resilient" is used to qualify such flexible features as generally returning to the initially molded shape without permanent deformation. As for the term "semi-rigid," this term is used to connote properties of support members that provide support and are free-standing, however such support members may have some degree of flexibility or resiliency.

B. Detailed Description of an Embodiment of a Diabetic Walker Having a Swivel Sole An embodiment of an orthopedic device or diabetic walker with easy access to a wound site and having many of the aforementioned attributes is disclosed in FIG. 1A. The walker 100 may be constructed in a manner similar to conventional walkers, as described in detail in U.S. Pat. Nos. 5,078,128, 5,329,705, and 5,378,223, and in U.S. publication no. 2004/0019307, previously incorporated by reference.

In particular, the walker 100 has at least one strut member 110 that extends vertically from a proximal portion of a base 120 of the walker. A typical configuration has two opposed strut members 110 that extend in the proximal direction from opposed sides of a base portion, or from two opposed base portions. The struts 110 and base 120 members may be made of any suitable rigid or semi-rigid material, for example aluminum, carbon/epoxy composites, glass fiber/epoxy composites, or plastic materials. The strut members 110 may be integrally formed with the base member 120 or with respective base members 120. Alternatively, the struts 110 may be separate members that are connected to the base member 120 or respective base members 120 via rivets, screws, adhesives, or any other suitable connection method.

Figure 1A:
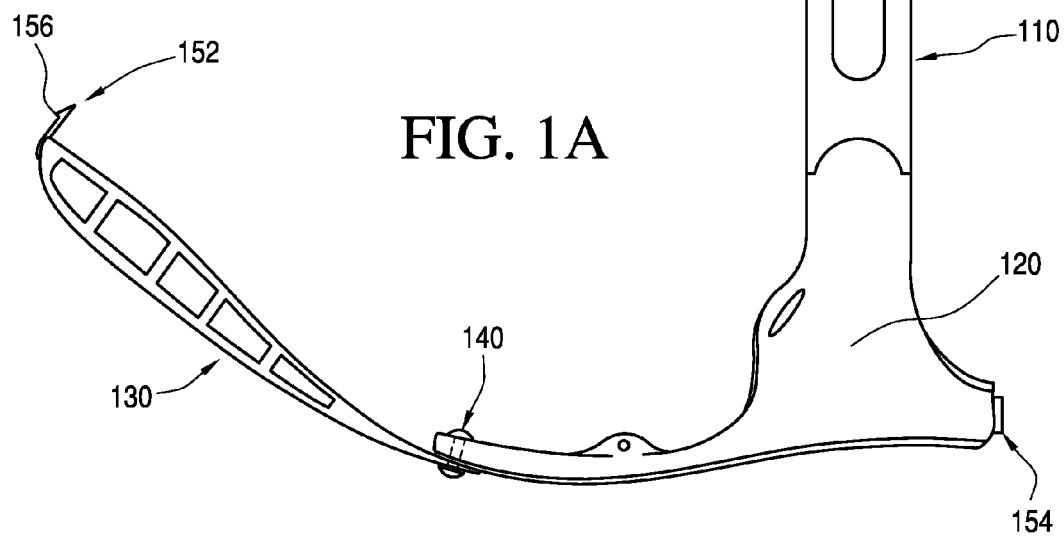
FIG. 1A is a side view of an embodiment of an orthopedic device with easy access to a wound site.
Figure 1C:
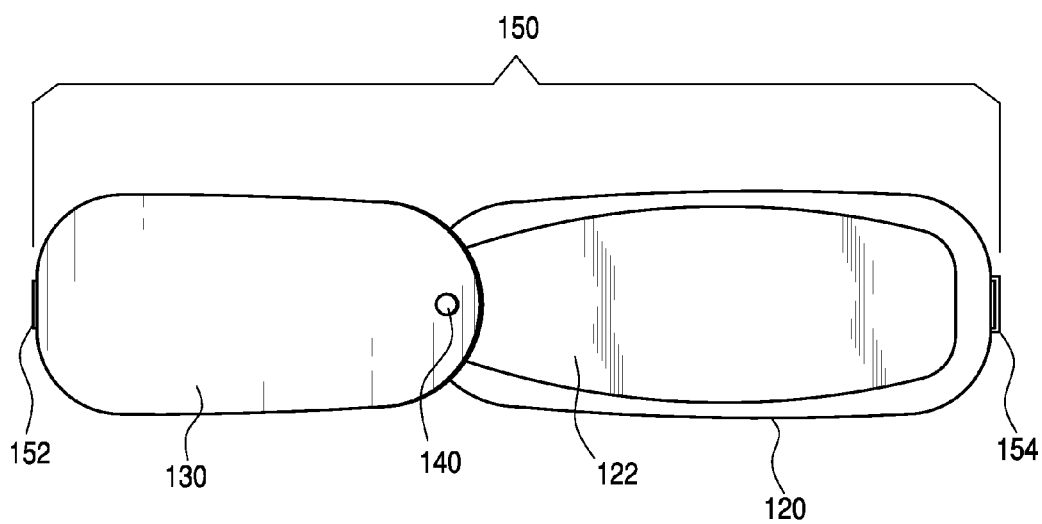
FIG. 1C is a bottom view of the embodiment of the orthopedic device as shown in FIG. 1A.

The base 120 has a foot receiving portion that extends in the anterior and posterior directions and is shaped and configured to receive and support a patient's foot therein, as shown in FIG. 1C. In order to allow access to the plantar surface of a patient's foot, an opening or window 122 is formed from and provided in the base 120. The opening 122 may extend along the entire plantar aspect of the foot, or may allow access to only a portion of the plantar surface of the foot.

The opening 122 may be integrally formed with the base 120, or the base 120 may be formed with a distal surface and the opening 122 may be cut, or otherwise provided, in the distal surface. For example, for a patient having ulcerations on only the ball portion of the plantar surface of the foot, the opening may be provided only in the area of the ball portion of the foot. However, an opening 122 providing access to the substantially the entire plantar surface of the foot allows the physician to inspect the entire plantar surface of the foot for signs of injury or disease.

In order to provide the function of a walker, a sole 130 is provided along the distal portion of the base or base members. The sole 130 may typically define a line of progression extending from a heel portion to a middle portion to a toe portion of the sole 130. The sole 130 may be constructed in any suitable manner from any suitable materials. The sole 130 may be made from a rigid or semi-rigid plastic and may have weight saving internal structures, such as openings or a box construction. If openings or a box structure are utilized, appropriate shock absorbing structures and materials may be utilized, such as a cantilevered heel portion having an absorbent material retained therein.

The sole 130 may also have a suitable curvature, such as a rocker sole, in order to control the gait mechanics of the leg that the walker 100 is attached to. The sole 130 may further have any suitable frictional or grip enhancing feature along the distal surface of the sole 130, such as friction ridges or a friction coating.

In order to make use of the opening 122 defined by the base or base members 120 around the plantar surface of the foot, the sole 130 is movable with respect to the base 120 and strut 110 members. In the exemplary embodiment of FIG. 1A, the sole 130 is connected to the base member 120 at connection member 140, which is a low profile rivet that allows the sole 130 to rotate in a clockwise or counterclockwise manner. In this manner, the sole 130 may be rotated or swiveled away from the plantar surface of the foot in order to allow a physician to inspect and treat any wounds thereon. This can be accomplished without having to remove the walker 100 from the patient's leg.

In order to maintain the sole 130 in position to support the walker 100 on the ground or a supporting surface, a locking mechanism 150 is provided. The locking mechanism includes a first portion 152 in the form of a latch. The latch member 152 is positioned on a posterior portion of the sole 130. A corresponding second portion 154 in the form of a housing defining a recess is provided on a posterior portion of the base 120 or base members 120. The latch member 152 is a resilient member that passes through the recess of the housing 154 and has a projection 156 thereon for selectively engaging a surface of the housing 154 in a manner that will be recognized by a skilled artisan.

As an alternative, as shown in FIG. 1B, a locking mechanism 160 may be provided. A latch member 162, similar to latch 152, is provided for being received within a housing 164. The latch member 152 has a projection 166 thereon for selectively engaging a surface within the housing. The housing 164 may have a resilient wall portion defining a release mechanism or a button 168 having a projection 169 thereon.

When the release mechanism or button 168 is actuated the projection 169 of the housing 164 may engage the projection 166 of the latch member 162 in order to disengage the projection 166 from the internal surface of the housing 164.

While the exemplary embodiment of FIG. 1A shows the connection 140 along an anterior portion of the walker 100 and the locking mechanism 150/160 along the posterior of the walker 100, it will be understood that the positions of the connection member 140 and the locking mechanism 150/160 may be modified, such that the connection member 140 is located along the posterior of the walker 100 and the locking mechanism 160 is positioned along the anterior of the walker 100. It will be further understood that the position of the latch member 152 and the housing member 164 may also be interchanged, such that the latch member 152 is located on the base portion 120 and the housing is located on the sole member 130.

In use, the walker 100 is attached to a patient's leg in a known manner using any suitable straps and attachment mechanisms. In order to support the attachment, suitable slots and connecting portions for straps and D-rings may be provided on the walker, as shown in FIG. 1A. Additionally, casting tape or any other suitable retaining mechanism, as will be discussed in more detail below, may be provided to essentially lock the walker 100 to the patient's leg, thus creating a diabetic walker that the patient may not remove without the assistance of a clinician.

A suitable insole or cushion may be provided within the opening 122 between the plantar surface of the foot and a proximal surface of the sole 130. The insole or cushioning may define the contact surface of the diabetic walker 100. The insole or cushion may be a gauze material, a foam pad, or other viscoelastic and protective material. Alternatively, the proximal surface of the sole 130 may define the contact surface for contacting the plantar aspect of the foot. The insole or cushion may be easily removed and replaced through the opening 122 in order to allow the physician or practitioner to inspect and treat the plantar surface of the patient's foot.

To engage the sole 130 in a position covering the opening 122, the sole 130 is rotated or swiveled into an aligned position with the base 120 such that the first and second portions 152, 154 of the locking mechanism 150 are aligned. The latch member 152 is then inserted into the recess of the housing 154 and the sole 130 is pushed in the proximal direction towards the base 120 in order to lock the sole 130 and the base 120 together. In this manner, the patient may utilize the walker 100 in the appropriate manner by walking on the sole 130.

When it is time for the patient's daily or weekly appointment to check the status of any wound or plantar ulceration, instead of removing the entire walker 100 from the patient's leg, the sole 130 may be swiveled such that the opening 122 is uncovered, and the physician may inspect and treat the plantar surface of the foot. In order to rotate the sole 130 so that the opening 122 is uncovered, the projection 156 of the latch 152 is pressed in order to disengage from the housing 154 and the sole portion 130 is pulled in a distal direction away from the base member 120 or members 120. Once the locking mechanism 150 is disengaged, the sole 130 may be rotated clockwise or counter-clockwise in order to uncover the opening 122.

Once the clinician has inspected and treated any wounds, the sole 130 may be rotated and locked back into position covering the opening 122, as discussed above. This configuration allows the physician or practitioner easy access to the plantar surface of the patient's foot, without requiring the time intensive and relatively costly removal and reapplication of the walker 100.

While the connection member 140 is illustrated as a rivet, any suitable connection that would allow the sole 130 to be rotated or swiveled to cover and uncover the opening 122 may be utilized. Further, while the sole 130 is illustrated as being maintained in a connected manner to the base 120 while in a position uncovering the opening 122, the sole 130 may alternatively be rotated and removed for example by providing two connected, appropriately sized bores through the sole 130, such that the rivet head may pass through one of the bores in a manner that will be apparent to the skilled artisan. Suitable connection mechanisms may be provided so as not to protrude from the proximal or distal surfaces of the sole 130, such that the connection mechanism does not interfere with the contact surface or with the interface between the sole 130 and the supporting surface or ground.

In an alternative construction, the sole 130 may be formed in two parts, an anterior portion and a posterior portion. Each of the anterior and posterior portions may be rotatably connected to the base 120 in a manner as discussed above, so that the toes and forefoot or the arch and heel may be selectively exposed by rotating the appropriate portion of the sole 130.

Other configurations falling within the scope of this disclosure will be readily apparent to a skilled artisan. Further exemplary embodiments are discussed below.

C. Detailed Description of Two Embodiments of a Diabetic Walker Having Hinged Soles An alternative embodiment of a diabetic walker 200 is shown in FIGS. 2A and 2B. Similar to the walker of FIGS. 1A and 1C, the walker 200 includes strut members 210 extending in the proximal direction from a base portion 220, which defines an opening (not shown, see FIG. 1C) for allowing access to the plantar surface of a foot.

The walker 200 also similar has a sole 230 that is moveable with respect to the base 220 and strut members 210. In this case, the sole 230 is rotatably connected to the base portion 220 via a hinge mechanism 240 located at the posterior portion of the sole 230 and the base 220. In this manner, the sole 230 may be rotated from the base 220 in order to allow a physician or practitioner access to the plantar surface of the foot without having to remove the entire walker 200. Any suitable hinge may be utilized, such as a swing hinge, so long as the sole 230 may be rotated from the base 220 in order to provide access to the plantar surface of the foot. Of course, the hinge 240 may be provided in any suitable position, other than as illustrated in the posterior, such as the anterior, or lateral or medial sides of the walker 220.

Locking mechanisms 250 are provided along lateral and medial sides of the walker 200. The locking mechanisms may be of any suitable type, such as those previously described or may, as illustrated, have a first latching portion 252 including a protrusion or biased button thereon. The latching portion 256 may be located along the lateral and medial sides of the sole member 230, as illustrated, or alternatively along the base portion 220. Correspondingly located second recess and/or biased button portions 254 are located along either the base portion 220 or the sole portion 230 for selectively engaging the first latching portions 252 in a manner that will be recognized by a skilled artisan.

Of course, the locking mechanisms 250 may be located in any suitable position, such as along the anterior or posterior of the walker 200. Further, the position of the first and second portions 252, 254 of the locking mechanism 250 may be swapped from the sole 230 to the base 220, and vice versa. It will further be recognized that any suitable number of the illustrated locking mechanisms 250 may be used.

Slots or D-ring attachment points 270, 280 are positioned on the base 220 for providing anchors or attachment points for straps and/or buckles in a manner that will be recognized by a skilled artisan.

A suitable insole or cushion 260 is provided within and covering the opening between the plantar surface of the foot and a proximal surface of the sole 230. The insole or cushion may define the contact surface of the diabetic walker 200. The insole or cushion may be a gauze material, a foam pad, or other viscoelastic and protective material. The insole 260 may be easily removed and replaced through the opening in the base 220 in order to allow access to the plantar aspect of the foot.

The function of the walker 200 is essentially similar to the manner in which the walker of FIGS. 1A and 1C is used. To lock the sole 230 in a position covering the opening, the sole 230 is rotated towards the base 220 and the protrusions or biased buttons 256 of the latch members 252 are engaged with the recesses/release buttons 254. To release the sole 230 from the locked position, the protrusions 256 or release buttons 254 are pressed and the sole 230 is rotated away from the base 220.

The embodiment as shown in FIG. 2B is similar in all respects to the embodiment of FIG. 2A, with the exception of the structure of the hinge mechanism 240. Instead, hinge mechanism 242 is provided. Hinge mechanism 242 may be an injection molded plastic living hinge of a type known to the skilled artisan. The hinge mechanism 242 allows the sole 230 to be rotated away from the base 220 in the same manner as hinge mechanism 240. Of course the hinge mechanism 242 and the locking mechanisms 250 may be provided in alternative locations along the base 220 and sole 230.

The hinge mechanisms 240, 242 allow the sole 230 to be rotated completely away from the plantar surface of the foot so that the clinician may examine and treat any wounds or plantar ulcerations. The hinge mechanisms 240, 242 provide a convenient alternative to the previously discussed connection mechanisms. The hinge mechanisms 240, 242 also provide the practitioner with the ability to slowly pull the sole 230 away from the plantar surface of the foot so that the plantar surface of the foot is not further damaged or irritated by the movement.

A variation of the rotatable sole embodiments of a diabetic walker is described next with a removable sole.

D. Detailed Description of an Embodiment of a Diabetic Walker Having a Removable Sole In an alternative embodiment of a diabetic walker 300 shown in FIG. 3, similar to the walker of FIGS. 1A and 1C, the walker 300 includes strut members 310 extending in the proximal direction from a base portion 320, which defines an opening (not shown, see FIG. 1C) for allowing access to the plantar surface of a foot.

A removable sole 330 is provided for selective attachment to the base 320. A locking mechanism 350, having a first portion or latch 352 with a projection 356 and a second portion or housing 354, as discussed above with reference to FIGS. 1A-B, is provided along a posterior portion of the base 320 and the sole 330.

Channel guides 332 are positioned along the lateral and medial sides of the sole 330 for aligning with and engaging slide members 322 positioned along lateral and medial sides of the base 320. An additional slide member 322 and channel guide 332 are respectively located along the anterior portions of the base 320 and the sole 330. The slide members 322 and channel guides 332 provide proper positioning and engagement between the base 320 and the sole 330.

A suitable insole or cushion 360 may be provided within and covering the opening between the plantar surface of the foot and a proximal surface of the sole 330. The insole or cushion may define the contact surface of the diabetic walker 300. The insole or cushion may be a gauze material, a foam pad, or other viscoelastic and protective material. The insole 360 may be easily removed and replaced through the opening in the base 320 in order to allow access to the plantar aspect of the foot.

Slots or D-ring attachment points 370, 380 are located on the base 320 for providing anchors or attachment points for straps and/or buckles in a manner that will be recognized by a skilled artisan.

In order to attach the sole 330 to the base 220, the practitioner locates the anterior slide member 322 of the base 320 within the anterior channel guide 332 of the sole and lines up the lateral and medial slide members 322 of the base 320 within the lateral and medial channel guides 332. The practitioner then rotates the sole 330 towards the base 320 until the sole 330 engages the base 320 and the locking mechanism is engaged to lock the sole 330 in a position covering the opening in the base 320. The process is reversed by pressing the projection 356 of the locking mechanism and rotating the sole 330 away from the base 320.

Of course, as discussed above, the locking mechanism 350 may be located along any portion of the walker 300, and the slides 322 and channel guides 332 may be appropriately repositioned. Further, additional or alternative locking mechanisms may be used.

The removable aspect of the sole 330 may allow for the use of different soles during the course of the treatment. For example, the curvature of the rocker sole may be varied from sole to sole in order to fine tune the gait mechanics of the leg utilizing the diabetic walker 300.

Having described embodiments of a diabetic where the sole member is rotatably moveable with respect to the base and strut members, a number of embodiments where the sole is slidingly moveable/removable with respect to the base and strut members are discussed next.

E. Detailed Description of an Embodiment of a Diabetic Walker Having a Slidably Removable Sole In an alternative embodiment of a diabetic walker 400 shown in FIGS. 4A and 4B, similar to the walker of FIGS. 1A and 1C, the walker 400 includes strut members 410 extending in the proximal direction from a base portion 420, which defines an opening (not shown, see FIG. 1C) for allowing access to the plantar surface of a foot.

A removable sole 430 is provided for selective attachment to the base 420. A locking mechanism 450, having a first portion or latch 452 having a projection 456 and a second portion or housing 454 is located along a posterior portion of the base 420 and the sole 430. A channel 458 is provided in the base 420 for receiving a portion, such as a flared projection or a key, of the first portion or latch 452. The channel 458 allows the first portion or latch 452 to be slid therein in order to allow a distal-proximal movement of the first portion or latch 452. In this manner, the first portion or latch 452 may be slid into and out of engagement with the second portion or housing 454. The projection 456 provides an actuating surface for the practitioner's finger for sliding the first portion or latch 452.

Figure 4B:
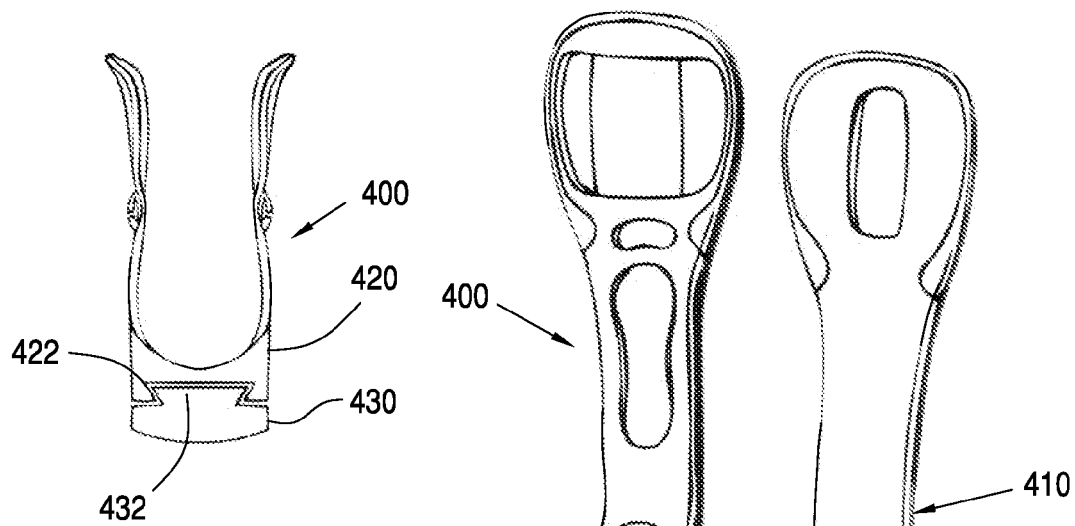
FIG. 4B is a rear view of the embodiment of the orthopedic device as shown in FIG. 4A with the locking structure removed for ease of illustration.
Figure 4A:
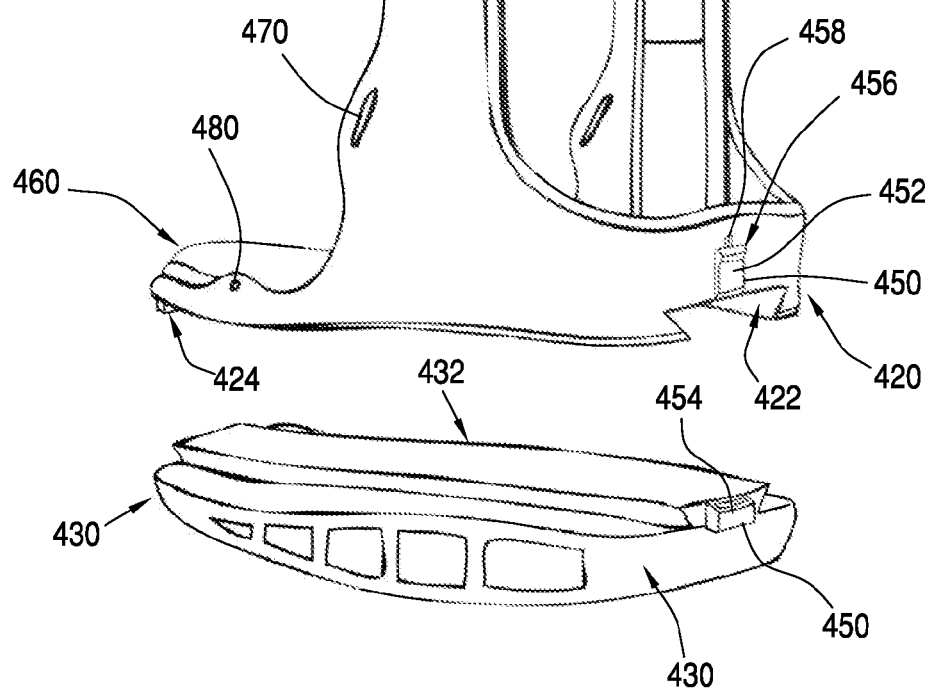
FIG. 4A is a side perspective view of another embodiment of an orthopedic device with easy access to a wound site.

A shaped portion or guide 422 is provided in the distal portion of the base 420 for selectively engaging a slide 432 on the proximal surface of the sole 430. The guide 422 and the slide 432 are correspondingly and complementary shaped, and extend in the anterior and posterior direction of the base 420 and the sole 430. As illustrated in FIG. 4B, the guide 422 and the slide 432 have complementary shaped trapezoidal configurations. While the guide groove 422 and the slide 432 are shown having a trapezoidal shape, it will be understood that any suitable shape may be provided, such as flanged or flared portions along a rectangular slide being received in correspondingly shaped recesses along the guide groove.

A stop member 424 is positioned on the base 420 along the anterior portion, in an opposed relationship to the locking mechanism 450. Of course, it will be recognized that the stop member 424 may be provided on the posterior portion of the base and that the locking mechanism 450 may be provided in an opposed position on the anterior portion of the base 420 and the sole 430.

The stop member 424 limits the movement of the slide 432 of the sole 430 within the guide 422 of the base 420. In this manner, the sole 430 will always be properly positioned on the base 420 such that the locking mechanism 450 may be easily engaged to lock the sole 430 onto the base 420.

Similar to embodiments discussed above, slots or D-ring attachment points 470, 480 are positioned on the base 420 for providing anchors or attachment points for straps and/or buckles in a manner that will be recognized by a skilled artisan.

Also as discussed above, a suitable insole or cushion 460 may be provided within and covering the opening between the plantar surface of the foot and a proximal surface of the sole 430. The insole or cushion may define the contact surface of the diabetic walker 400. The insole or cushion may be a gauze material, a foam pad, or other viscoelastic and protective material. The insole 460 may be easily removed and replaced through the opening in the base 420 in order to allow access to the plantar aspect of the foot.

In use, to attach the sole 430 to the base 420, the anterior portion of the slide 432 is inserted into the posterior portion of the guide 422. The sole 430 is then moved in the anterior direction until the anterior portion of the sole 430 contacts the stop member 424. The first portion or latch 452 of the locking mechanism is now positioned so that it may be slid into the engagement with the second portion or housing 454.

To remove the sole 430, the process is reversed. The first portion or latch 452 of the locking mechanism 450 is slid out of engagement with the second portion or housing 454. The sole 430 can then be slid in the posterior direction until the slide 432 is disengaged from the guide 422. At this time, the insole or cushion 460 and any gauze, pads, or ointments may be removed from the plantar surface of the foot through the opening in the base 420. Thus, the plantar surface of the foot is exposed for examination and treatment.

The structure of the guide 422 and the slide 424 provide a secure fit between the sole 430 and the base 420, due to the increased size of the surface area of the engaging surfaces of the sole 430 and the base 420. Thus, it is less likely that the sole 430 may become accidentally disengaged from the base 420, unless extreme forces are applied to the base 420 and the sole 430.

Next, another form of removable sole for a diabetic walker is described.

F. Detailed Description of Another Embodiment of a Diabetic Walker Having a Removable Sole Similar to the embodiment discussed above, an alternative embodiment of a diabetic walker 500 having struts 510 extending in the proximal direction from a base 520 and a removable sole 530 is illustrated in FIG. 5. As discussed with other embodiments, the base 520 defines an opening (not shown, see FIG. 1C) for allowing access to the plantar surface of a foot.

Similar to embodiments discussed above, slots or D-ring attachment points 570, 580 are positioned on the base 520 for providing anchors or attachment points for straps and/or buckles in a manner that will be recognized by a skilled artisan.

Also as discussed above, a suitable insole or cushion (not shown) may be provided within and covering the opening between the plantar surface of the foot and a proximal surface of the sole 530. The insole or cushion may define the contact surface of the diabetic walker 500. Alternatively, the proximal surface of the sole 530 may define the contact surface of the diabetic walker without requiring an additional insole or cushion member. The insole or cushion may be a gauze material, a foam pad, or other viscoelastic and protective material. The insole may be easily removed and replaced through the opening in the base 520 in order to allow access to the plantar aspect of the foot.

At least one clip member 522 may be provided along the lateral and/or the medial sides of a distal portion of the base 520. As illustrated, a number of clip members 522 are provided in a spaced apart relationship along the distal portion of the base 520. The clip members 522 may have a first portion that extends distally from the distal portion of the base 520 and a second portion that extends towards the posterior of the walker 500 in order to define an "L-shape." Of course, the second portion may alternatively extend towards the anterior of the walker 500.

The clip members 522 are shaped and configured to selectively engage with recesses or clip housings 532 positioned within the sole 530 along lateral and/or medial sides of the sole 530. The clip housings 532 are correspondingly shaped to the clip members 522, such that the clip members 522 may be received within the clip housings 532. Thus, as shown, the clip housings 532 have a first portion that extends distally into the sole 530 from the proximal surface of the sole 530 and a second portion that extends towards the posterior of the walker 500. Of course, if the second portion of the clip members 522 extends towards the anterior of the walker 500, the second portion of the clip housings 532 would also extend towards the anterior of the walker.

In use, in order to engage the sole 530 with the base 520, the sole 530 distally positioned with respect to the base 520 so that the clip members 522 are aligned with the clip housings 532. The sole 530 is next moved in the proximal direction towards the base 520 such the clip members 522 are received within the first portion of the clip housings 532. Once the distal surface of the base 520 and the proximal surface of the sole 530 are brought into flush engagement, the sole 530 or the strut 510 and base portion 520 are respectively moved in an anterior or posterior direction such that the second portion of the clip members 522 is received within the second portion of the clip housings 532. In this manner, the sole 530 is locked onto the base 520. In order to unlock the sole 530 from the base 520, the process is simply reversed.

Of course, an additional locking mechanism, such as any one of those previously or hereinafter discussed may also be provided in addition to the clip members 522 and the clip housings 534. Such an additional locking mechanism may be positioned in any appropriate manner on the walker 500, as discussed in detail above and below.

Further, it will be recognized that any suitable number of clip members 522 and clip housings 532 may be utilized within the scope of the pending embodiments. Additionally, the positioning of the clip members 522 and clip housings 532 located along the anterior and posterior direction of the walker 500 may be configured in any suitable position. For example, clip members 522 and clip housings 532 may be provided along substantially the entire length of the base portion 520 and the sole member 530. Alternatively, a few clip members 522 and clip housings 532 may be provided along just the anterior and posterior portions of the base 520 and the sole 530.

It will also be recognized that alternative shapes may be provided for both the clip members 522 and the clip housings 532. For example, the clip members 522 may be have a "J-shape" where the first and second portions of the clip members 522 are integrally formed with a distally extending portion and a curved portion. The clip housings 532 may be in the form of a recess having a strut or rod extending across the recess for engaging the curved portion of the "J-shaped" clip members 522. Additionally, the size of the clip members 522 and the clip housings 532 may be any appropriate size, and may vary according to any number of factors, such as the number of clip members 522 and clip housings 532, or the weight of the patient.

Accordingly, the embodiment shown in FIG. 5 allows the sole 530 to be removed so that a clinician may examine and treat the plantar surface of the patient's foot, without having to remove the walker 500 from the patient's limb. The structure also allows soles to be interchangeable, such that soles having different characteristics may be provided to the walker 500 without having to remove the walker 500 from the patient's leg.

Next, alternative forms of removable soles for a diabetic walker are described.

G. Detailed Description of Alternative Embodiments of Diabetic Walkers Having Removable Soles Alternative embodiments of a diabetic walker 600, 700 are shown in FIGS. 6 and 7. In these embodiments, strut members 610, 710 extend from base portions 620, 720. The strut members 610, 710 and base portions 620, 720 may be integrally formed or coupled together. The base portions 620, 720 also include a retaining strap member 622, 722 for maintaining the walker 600, 700 in position on the patient's limb. Exemplary retaining straps are further described below. The base portions 620, 720 define lateral and medial flange or wing portions. The base portions 620, 720 may be formed from a resilient material in order to allow the flange or wing portions to be pulled away from the patient's foot and to return to the original configuration when the pulling force is released. The distal portions of the base portions 620, 720 and flange or wing portions are complementary formed to engage a proximal portion of a sole member 630, 730.

The sole members 630, 730 are be formed in two portions, an upper sole or insole portion 640, 740 and a lower sole or rocker portion 650, 750. The sole members 630, 730 are selectively engageable with the base portions 620, 720, and the two portions, 640, 740 and 650, 750 of the sole members 630, 730 are selectively engageable with each other.

Locking structures are positioned on the base portions 620, 720 and the upper sole portions 640, 740 in order to provide selective engagement between the base portions 620, 720 and the upper sole portions 640, 740. With regard to the embodiment of FIG. 6, posterior lock members 624 are provided on an anterior surface of the posterior portion of the base portion 620. The lock members 624 each have a first portion that extends in the anterior direction away from the base portion 620. A resilient locking projection extends distally from the anterior end of the first portion of each locking member 624.

Additional slide lock members 626 that extend in the anterior and posterior direction along inner lateral and medial sides of the base portion 620 are also provided in order to aid with selectively engaging the base portion 620 to the sole portion 630. The slide lock members include projections along an anterior portion thereof for selectively engaging the sole member 630, as will be discussed below. In alternative embodiments, the slide locks 626 may extend in the proximal and distal direction.

The upper sole portion 640 is provided with the corresponding locking mechanisms for engaging the posterior 624 and slide lock members 626 of the base portion 620. Recesses or slots 644 for receiving, or allowing the posterior lock members 624 to pass through are positioned along a posterior portion of the upper sole portion 640. The resilient locking projection of the posterior lock members 624 engages a lip formed by the slots 644 in a snap engaging manner. Further slots 646 are provided along the outer lateral and medial sides of the upper sole portion 640 for receiving therein the slide lock members 626.

The slots 646 extend from substantially the posterior portion of the upper sole 640 for a predetermined length such that the slide lock members 626 may be received therein. In an alternative embodiment the slots 646 may extend in the proximal and distal direction to engage correspondingly oriented slide locks. A deeper recessed portion may be provided at the anterior ends of the slots 646 for receiving the projections of the slide lock members 626.

In order to join the base portion 620 with the sole member 630, the slide lock members 626 and the base portion 620 are aligned with the slots 646 and the sole member 630. The base portion 620 and the sole 630 are respectively or simultaneously moved in the anterior or the posterior direction until the projections on the slide locks 626 are received within the deeper portions of the slots 646 and the posterior locks 624 are received within or engage the slots 644.

In order to separate the base portion 620 from the sole member 630, the wing or flange portions of the base portion 620 are pulled away from the sole 630 and the patient's foot until the projections on the slide locks 626 are removed from the deeper portions of the slots 646. A force may then be applied in the posterior direction to the base portion 620 or the anterior direction to the sole member 630 in order to cause the posterior lock members 626 to disengage from the recesses or slots 644. The base portion 620 and the sole 630 are then respectively or simultaneously moved in the posterior or the anterior direction in order to separate the base portion 620 from the sole member 630. In this manner, the plantar surface of the foot may be exposed for examination and treatment.

In addition to the selective engagement between the base 620 and the sole 630, the upper sole 640 and the rocker sole 650 are also selectively engageable. A rocker sole clip 642 is provided on the posterior portion of the upper sole 640 for receiving therein a rocker sole latch (see element 752, FIG. 7) that is positioned on the posterior portion of the rocker sole. This configuration functions in a similar manner to locking mechanisms previously discussed. In fact, the rocker sole clip 642 and rocker latch may be configured as an additional locking mechanism for maintaining the base 620 in engagement with the sole 630 by simply providing the rocker sole clip 642 on the posterior portion of the base 620 instead of the posterior portion of the upper sole 640.

The arrangement of the embodiment of FIG. 6 allows the practitioner or physician to selectively examine the plantar surface of the patient's foot without removing the strut 610 and base portion 620 from the patient's limb, or to replace the rocker sole 650 with a rocker sole having different characteristics without having to remove the entire sole assembly 630.

In a similar configuration, shown in FIG. 7, the base portion 720 is provided with posterior lock members 724 that are located on the exterior, posterior portion of the base 720 and that extend distally from the distal portion of the base portion 720. The posterior lock members 724 each have a projection positioned along the distal end of the lock members 724 for snap engagement with a corresponding portion of the sole 730, as discussed further below. The posterior lock members 724, or at least the projections, may be resiliently formed so as to allow the lock members to be selectively moved to allow engagement and disengagement with the sole member 730 and to return to their original shape.

Additional lock mechanisms in the form of hook members 726 are provided distally extending from an anterior, distal portion flanges or wings of the base portion 720. The hook portions of the hook members 726 extend towards the posterior of the base portion 720. The sole member 730 includes correspondingly located and shaped structures for engaging the base member 720, as will be discussed below.

As discussed above with respect to the embodiment of FIG. 6, the sole 730 of the embodiment shown in FIG. 7 includes an upper sole or insole portion 740 that is selectively engageable with a rocker sole portion 750 in the same manner as discussed above with respect to the embodiment of FIG. 6. That is the upper sole carries a rocker sole clip 742 for receiving a rocker sole latch 752 therein. Both the rocker sole clip and the rocker sole latch are provided in the posterior portion of the sole 730. In an alternative embodiment, the rocker sole clip 742 may be provided on the base portion 720 in order to perform as an additional locking mechanism.

Posterior lock receivers 744 are positioned in the posterior portion of the upper sole 740 on either side of the rocker sole clip 742. The posterior lock receivers 744 are in the form of bands defining a recess between the bands and the upper sole 740 for receiving the posterior lock members 724 therein. Slots 746 are located along lateral and medial sides of the proximal portion of the upper sole 740. As shown in FIG. 7B, the slots 746 have an opening that receives the hook members 726, and a hollowed out portion extending to the posterior of the opening to allow the extending portion of the hook members 726 to be lockingly received therein.

In use, the base portion 720 is aligned with the sole member 730 such that the hook members 726 are positioned proximally over the slots 746. The base portion 720 and the sole member 730 are then brought together such that the hook members 726 are then received within the slots 746. The base portion 720 and the sole member 730 are then moved relative to each other such that the extending portion of the hook members 726 is received within the extending portion of the slots 746 to provide a locking engagement between the hook members 726 and the slots 746.

Once the hook members 726 are engaged with the slots 746, the posterior lock members 724 are inserted through the recesses defined by the posterior lock receivers 744 by moving the base portion 720 distally towards the sole member 730, and/or the sole member 730 proximally towards the base portion 720. The projections of the posterior lock members 724 lockingly engage the bands of the posterior lock receivers 744 in order to maintain the base portion 720 engaged with the sole member 730.

In order to disengage the base portion 720 from the sole member 730, the process is reversed. Both of the projections of the posterior lock members 724 are displaced towards the sole member 730 in order to allow the projections to pass through the recesses defined by the bands of the posterior lock receivers 744. The base 720 may then be pulled away from the sole 730 to disengage the posterior lock members 724 from the posterior lock receivers 744. The base 720 and the sole member 740 may then be moved relative to each other in order to disengage the hook members 726 from the slots 746 such that the base 720 may be completely disengaged from the sole 730. Thus, in this manner the plantar surface of the patient's foot may be exposed for examination and treatment in a quick and easy manner without having to remove the walker 700 from the patient's limb.

Additionally, the embodiment of the diabetic walker 700 of FIG. 7 allows the physician to remove the sole 730 with little or no frictional shear between the sole 730 and the plantar surface of the foot. Thus, there is little risk that the existing wounds or plantar ulcerations will be further damaged by the removal. There is also reduced risk of creating new wounds by removing the sole 730.

Further embodiments of diabetic walkers are discussed below where the base and sole may be removed from a strut assembly or strut members.

H. Detailed Description of Embodiments of a Diabetic Walker Having Separable Soles and Strut Assemblies In the alternative embodiments of diabetic walkers 800, 900 shown in FIGS. 8 and 9, the base portions 820, 920 may be integrated with the soles 830, 930, or formed in a unibody design, and a strut assembly or struts 810, 910 are selectively coupled and uncoupled from the base portions 820, 920 and sole members 830, 930, as will be discussed in more detail below.

Similar to embodiments discussed above, slots or D-ring attachment points 870, 970, 880, 980 may be located on the base 820, 920, or the struts 810, 910 for providing anchors or attachment points for straps and/or buckles in a manner that will be recognized by a skilled artisan.

Also as discussed above, a suitable insole or cushion 860, 960 may be provided within and covering the opening between the plantar surface of the foot and a proximal surface of the sole 830, 930. The insole or cushion may define the contact surface of the diabetic walker 800, 900. Alternatively, the proximal surface of the sole 830, 930 may define the contact surface of the diabetic walker without requiring an additional insole or cushion member. The insole or cushion may be a gauze material, a foam pad, or other viscoelastic and protective material. The insole may be easily removed and replaced from the base 820, 920.

Figures 8A, 8B:
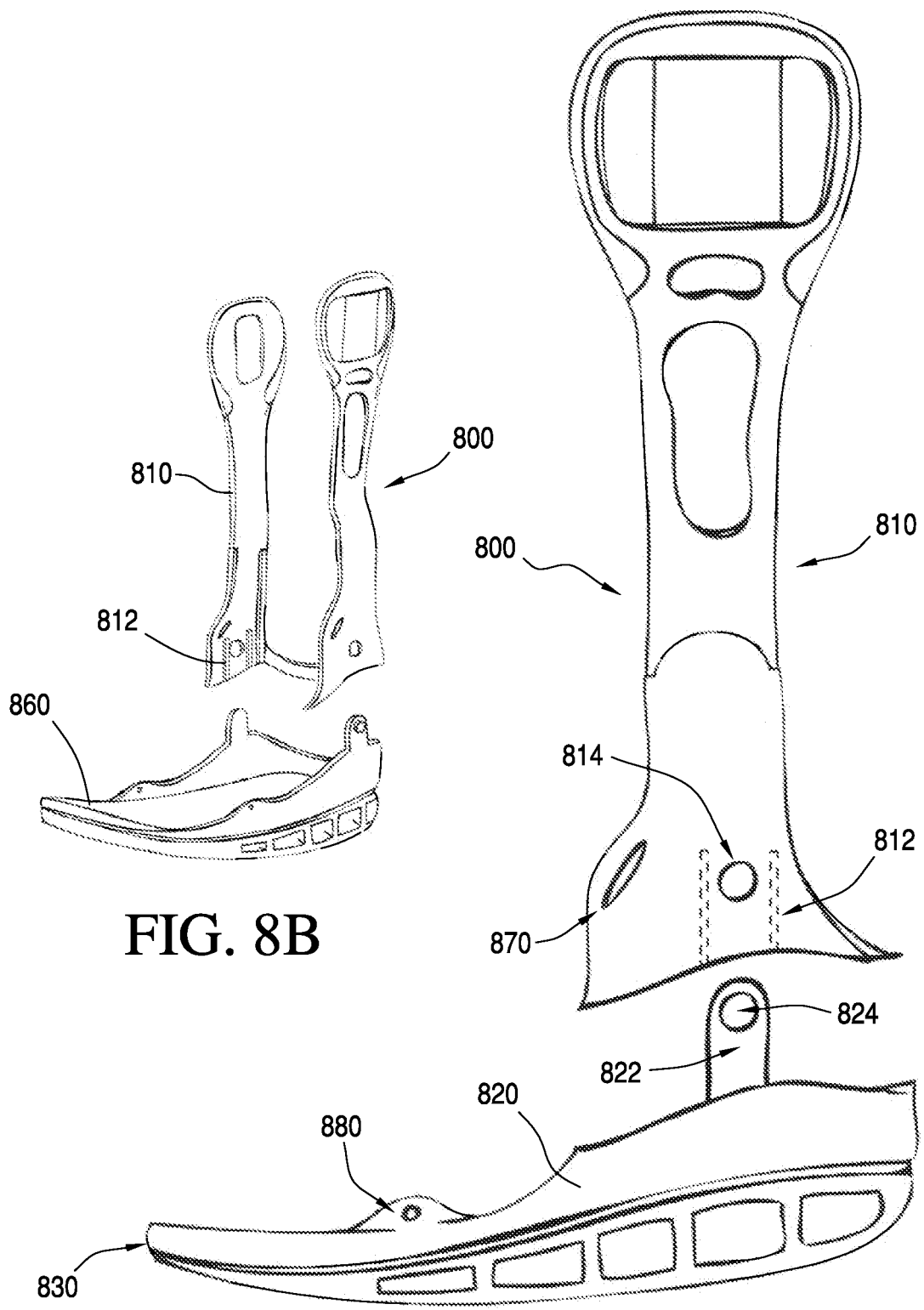
FIG. 8A is a side view of another embodiment of an orthopedic device with easy access to a wound site.
FIG. 8B is a perspective view of the embodiment of the orthopedic device as shown in FIG. 8A.

As shown in FIGS. 8A and 8B, a strut assembly 810 having at least one strut extending therefrom is provided in a selectively engageable manner with the base 820 and sole 830 of the walker 800. The strut assembly 810 includes an appropriately sized and shaped stiffening bar or rib extending to the posterior of, and joining, strut members. A portion of a locking mechanism in the form of guide members 812 extending in the proximal and distal directions is provided on inner lateral and medial surfaces of the respective struts. Two guide members 812 are provided on each inner lateral and medial surface spaced apart from each other in the anterior and posterior direction to define a receiving space therebetween. A hole, recess, or otherwise female lock receiving portion 814 is provided in the receiving space along a proximal end of the guides 814 for receiving a projection, button, or other male locking portion 824, as will be discussed in more detail below.

An extending portion 822 is provided in substantially the posterior portion of the walker 800 and extending in the proximal direction from a proximal portion of the base portion 820. The extending portion 822 is shaped and configured to engage and be guided by the guide members 812. The projection, button, or other male locking portion 824 is provided on, and extends from, the exterior lateral and medial surfaces of the respective extending portions 822 for releasable locking engagement with the hole, recess, or otherwise female lock receiving portion 814. The male locking portion 824 may also be a biased button or tab.

In order to join the strut assembly 810 to the base portion 820 and sole member 830, the extending portions 822 of the base 820 are aligned distally below the guide members 812, such that the extending portions are positioned within the receiving spaces defined between the guide members 812. Once the extending portions 822 are aligned with the receiving spaces, the strut assembly 810 and the base portion 820 and sole member 830 are relatively moved towards each other in the proximal and distal direction until the male locking or projection member 824 engages the recess or female lock receiving portion 814.

When the male locking or projection members 824 engage the recesses or female lock receiving portions 814, the strut assembly 810 is locked into engagement with the base portion 820 and sole member 830. It will be recognized that the strut assembly 810 and the extending portions 822 may be somewhat resilient in order to allow the strut assembly 810 and the base portion 820 and the sole member 830 to be more easily brought together. For example, the strut assembly 810 may be provided with some resiliency from the connecting support band. Alternatively, the struts themselves may be formed from a substantially rigid and resilient material.

In order to separate the strut assembly 810 from the base portion 820 and the sole member 830, the male locking or projection members 824 are actuated or pressed in order to disengage from the recesses or female lock receiving portions 814. When the male locking or projection members 824 are disengaged from the recesses or female lock receiving portions 814, the strut assembly 810 and the base portion 820 and sole member 830 may be moved away from each other in the proximal and distal direction. Thus, the strut assembly 810 is separated from the base portion 820 and the sole member 830. In this manner, the plantar surface of a patient's foot may be exposed for examination and treatment, without having to remove the entire walker 800 from the patient's limb. Since the base portion 820 and sole member 830 are pulled distally away from the plantar surface of the foot, there is little risk of additional damage to the plantar surface of the foot due to frictional contact with the sole member 830 or insole 860.

In a similar embodiment, as shown in FIG. 9, the walker 900 is provided with a unibody base portion 920 integrally formed with a rocker sole member 930. In place of the strut assembly are individual strut members 910. Of course, the strut members 910 may be connected in a similar manner as the strut assembly of the embodiment shown in FIG. 8. Hook and/or loop fastening mechanisms 914, such as VELCRO, are provided along the exterior lateral and medial surfaces of the strut members 910 in order to aid with the proper fit and adjustment of the walker 900 to the patient's limb.

Locking projections 912 are positioned along the distal ends of the struts 910 for releasably engaging the struts 910 to the base 920. The projections 912 are resilient projections having flared ends for engaging recesses or receiving holes 922 on the proximal portion of lateral and medial wing or flange portions along the posterior of the base 920. The projections 912 cooperate with the recesses or holes 922 in a snap engagement, such that the strut members 910 may be disengaged from the base portion 920. This may be accomplished by providing snap engaging portions within the recesses or holes 922 that selectively lock the flared ends of the projections 912 within the recesses or holes 922.

The joining and separation of the struts 910 and the base 920 is accomplished in a manner similar to those discussed above. In order to join the struts 910 and the base 920, the struts 910 and the base 920 are aligned such that the projections 912 are located proximally over the recesses or holes 922. Once the projections 912 are in position over the recesses or holes 922, the struts 910 and the base 920 are brought into engagement such that the projections 912 enter into the recesses or holes 922 and engage the snap engaging portions therein. A clicking sound may indicate that the struts 910 are properly locked in place.

In order to remove the struts 910 from the base 920, a force is applied in the proximal direction to each of the struts 910 until the projections 912 are released from the snap engaging portions within the recesses or holes 922. Thus, the entire plantar surface of the foot may be accessible for inspection and treatment without removing the strut members 910 of the walker 900 from the patient's limb.

Of course other locking arrangements, such as any one of the previously or hereinafter described embodiments, may be provided to the walkers 800, 900. For example, the extending portions may engage guide members that are located on the exterior lateral and medial surfaces of the struts.

It will be recognized that the position of the male and female locking portions may be alternated such that the male locking portion is positioned on the strut and the female locking portion is received on the base. Additional male and female locking members may be provided in order to provide secondary locks. Further, the struts may have an enlarged distal portion that is locked to the base portion with mechanical fasteners that require the use of an included tool to fasten and unfasten in order to separate the struts from the base.

While the base 820, 920 and sole 830, 930 of the walkers 800, 900 are shown to be integral with each other, a removable sole, such as any one of the previously or hereinafter described embodiments, may be provided to the walkers 800, 900.

Another embodiment of a diabetic walker having a removable sole is discussed below.

I. Detailed Description of an Embodiment of a Diabetic Walker Having a Removable Sole Another embodiment of a diabetic walker 1000 is shown in FIG. 10. In this embodiment, the walker 1000 includes opposed lateral and medial strut members 1010 that are integral with and extend from opposed lateral and medial base members 1020. The struts and base members 1010, 1020, have slots or attachment points 1070 for receiving or attaching straps therein for applying the walker 1000 to the patient's limb. At least one extension member 1022 extends from a distal portion of the base members 1020 and carries ratcheting projections 1024 along at least one surface thereof The strut and base members 1010, 1020 may be selectively connected to a sole member 1030. The sole member 1030 may have at least one extension member receiving slot 1032 positioned along the lateral and medial sides of the sole 1030 for receiving and selectively locking the extension member therein. This is accomplished by utilizing a selectively releasable ratchet mechanism that is retained within the sole 1030. The releasable ratchet mechanism includes a selective release mechanism 1034, such as a biased button, for disengaging the ratchet projections 1024 in a manner that will be recognized by the skilled artisan. The release mechanisms 1034 are located on the proximal surface of the sole member 1030. Alternatively, the release mechanisms 1034 may be located on the distal surface of the sole member 1030. Locking covers may be provided over the release mechanisms 1034 such that the patient may not unlock the ratchet mechanism.

An insole or cushion member may be provided along the proximal surface of the sole 1030 in order to define the contact surface for the plantar surface of the foot. The insole or cushion member may be positioned over the release mechanisms 1034 in order to protect the plantar surface of the patient's foot. Alternatively, the release mechanisms 1034 may be recessed below the proximal surface of the sole 1030, such that the proximal surface of the sole 1030 may define the contact surface for the plantar surface of the foot.

In order to attach the struts and base members 1010, 1020 to the sole member 1030, the struts and base members 1010, 1020 are positioned proximally over the sole member 1030 so that the extension members 1022 are aligned with the extension member receiving slots 1032. Once aligned, the struts and base members 1010, 1020 may be brought together with the sole member 1030 such that the ratchet projections 1024 are engaged with the ratchet locking mechanism.

In order to release the struts and base members 1010, 1020 from the sole member 1030, the release mechanisms 1034 are actuated in order to disengage the ratchet projections 1024, and the struts and base members 1010, 1020 and/or the sole member 1030 are moved in the proximal and distal directions relative to each other in order to remove the sole member 1030 from the struts and base members 1010, 1020. The release mechanisms 1034 may be actuated by sliding a tool or the practitioner's finger between the insole/cushion or foot of the patient and the proximal surface of the sole 1030. Alternatively, if the release mechanisms 1034 are located on the distal surface of the sole member 1030, the release mechanisms 1034 are simply actuated. In this manner, the plantar surface of the patient's foot may be exposed for inspection and treatment without removing the entire walker 1000 from the patient's limb, since the struts and base members 1010, 1020 may remain attached to the limb while the sole 1030 is removed.

Next, an alternative embodiment of a diabetic walker having a removable sole is discussed.

J. Detailed Description of an Embodiment of a Diabetic Walker Having a Removable Sole As shown in FIG. 11, a further alternate embodiment of a diabetic walker 1100 is provided.

In this embodiment, a body member 1120 is provided for engaging the dorsal aspect of the patient's foot, ankle, and lower leg. The body member 1120 may be an anterior shell having an appropriate "L-shape" in order to be complementary shaped to the dorsal aspect of the patient's foot, and the dorsum of the ankle and lower leg. The body member 1120 may include proximal and distal flange portions that extend around the ankle and leg in the posterior direction.

The body member 1120 may be formed from any suitable rigid, or substantially rigid and resilient material. For example, the body member 1120 may be formed from any appropriate thermoplastic or thermosetting polymer, carbon, carbon fiber epoxy composite, plastic, fiber reinforced plastic, molded chopped fibers, laminates, metal or any other suitable material. Other exemplary materials include, but are not limited to, nylons, glass filled nylon, polypropylenes, vinyls, polyvinyl chlorides, high density polyethylene, epoxies, urethanes, and polyesters. The body member 1120 may be formed in any suitable manner, for example injection molding, casting, or curing.

In order to facilitate proper fitting of the body member 1120 to the patient, a mechanism for custom fitting may be provided, for example serrated lines 1122 that define portions that may be removed in order to adjust the length of the body member 1120. The custom fitting mechanism may be raised guide lines, reduced thickness weakened portions, or any other suitable structure that allows the body member 1120 to be custom fit to the patient.

Proximal and distal posterior shell portions 1112 and 1116 are provided to engage the posterior calf and ankle portions of the patient in order to maintain the walker 1100 in position on the patient's limb. The shell portions 1112, 1116 may be made in the same manner and from the same materials as the body member 1120. The shell portions 1112, 1116 have an appropriate curvature in order to define flange portions that extend in the anterior direction to be engaged with the posterior extending portions of the body member 1120. In alternative embodiments, the distal shell portion 1116 may be integrally formed with, or otherwise permanently attached to the body member 1120.

A strut member 1110 is provided for extending between the proximal and distal shell portions 1112, 1116 in order to offer structural support to the posterior portion of the walker 1100. The strut member 1110 may be any suitable substantially rigid material, similar to the body member 1120.

The body member 1120 and the shell portions 1112, 1116 are selectively locked in order to attach the walker 1100 to the patient's limb in a manner that does not allow the patient to remove the walker in the absence of a practitioner. For example, first and second screw lock mechanisms 1114, 1118 are provided for respectively attaching the proximal and distal shell portions 1112, 1116 to the proximal and distal flange portions of the body member 1120. Of course, it will be recognized that any suitable locking mechanism, such as any of those described herein, may be utilized.

In order to provide further adjustment for a proper fit, the strut 1110 and shell portions 1112, 1116 may be attached to the body member 1120 in such a manner as to allow height adjustability. For example, multiple holes 1126 are provided in the proximal flange of the body member 1120. The holes 1126 extend in the proximal and distal directions. Thus, when the walker 1100 is assembled, the first locking mechanism 1114 passes through the appropriate hole 1126 in order to ensure that the walker 1100 has a proper fit. In this manner the proximal shell portion 1112 may be adjusted in the proximal and distal directions in order to accommodate different lengths of patient's legs.

The strut member 1110 also includes similar height adjusting structures in order to allow the shell portions 1112, 1116 to be adjusted on the strut member 1110.

A sole member 1130, such as a rocker sole, is also provided in order to define a contact surface for the plantar surface of the foot. Of course, any suitable insole or cushion may also be provided along the proximal surface of the sole member 1130 for defining the contact surface for the plantar surface of the foot.

The sole member 1130 is selectively, removably attached to the distal portion of the body member 1120, in order to provide access to the plantar surface of the patient's foot. The sole member 1130 may be formed from any of the same materials as the body member 1120.

A suitable locking mechanism is provided to selectively lock the sole member 1130 to the body member 1120. In the example shown in FIG. 11, slots 1124 are provided along lateral and medial sides of the distal portion of the body member 1120. Straps 1132 having suitable hook and loop fasteners, snap fasteners, buckles, or other suitable fasteners are provided along the medial and lateral sides of the proximal portion of the sole member 1130 for threading through the slots 1124 for fitting the sole member 1130 to the base member 1120. Of course, any suitable locking mechanism may be utilized, such as snap receivers on the body member 1120 for engaging snap fasteners on the straps of the sole member 1130. Any of the herein described locking mechanisms may also be used. It will be recognized that suitable locking mechanisms may be provided on the body member 1120 and the sole member 1130 in order to prevent the unauthorized removal of the walker 1100 by the patient without the presence of a physician.

In order to assemble the walker 1100, the sole member 1130 is positioned along the body member 1120 such that the straps 1132 are aligned with the slots 1124. The straps 1132 are then threaded through the slots 1124 and the fastening mechanism, such as hook and loops, is engaged to maintain the sole member 1130 in position.

The process of removing the sole member 1130 from the body member 1120 is simply the reverse. That is, the fastening mechanism is disengaged and the straps 1132 are removed from the slots 1124, such that the sole member 1130 may be removed from the body member 1120. In this manner, the plantar surface of the foot is easily exposed for inspection and therapy, without having to remove the entire walker 1110 from the limb of the patient. This embodiment also provides for device customization from patient to patient.

Next, an embodiment of a sole assembly for use with a diabetic walker having a removable sole is discussed.

Figure 12:
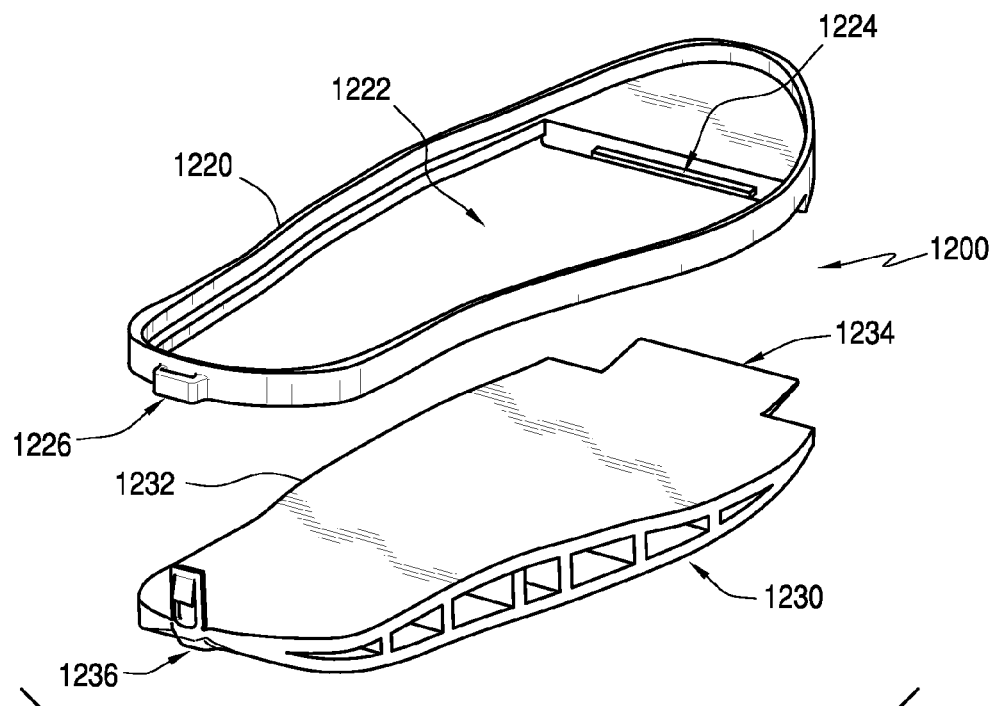
FIG. 12 is a perspective view of another embodiment of a sole assembly for an orthopedic device.

K. Detailed Description of an Embodiment of a Sole Assembly for use with a Diabetic Walker As shown in FIG. 12, a sole assembly is provided for use with any of the disclosed embodiments, for example the embodiments shown in FIGS. 6 and 7. The sole assembly 1200 includes a base portion 1220 and a sole member 1230 that are selectively joinable. The base 1220 may be provided as an insert for an open end of an off-loading walker type orthopedic device. Alternatively, the base 1220 may be integrated as the open end of a walker type orthopedic device, with the opening 1222 in the base 1220 serving as the opening for allowing inspection and treatment of the plantar surface of the patient's foot.

The base portion 1220 generally conforms to the outline of a patient's foot and to the distal portion of a walker. An opening 1222 is provided within the base member 1220. A platform that defines a sole receiver or lip 1224 is provided in the anterior portion of the base portion 1220 for use in retaining the sole member 1230 connected to the base portion 1220, as will be discussed further below. A housing or latch receiving portion 1226 is provided on the exterior, posterior portion of the base 1220 for engaging a latch 1236 of the sole member 1230, as will be further discussed below.

The sole member 1230 is generally complementary shaped and configured to close the opening 1222 when the sole member 1230 is connected to the base 1220. The sole member 1230 includes a sole insert or lip 1234 that projects from an anterior portion of the sole member 1230. A latch or locking member 1236 is provided along the posterior portion of the sole member 1230.

The sole member 1230 is engaged with the base 1220 in the following manner. The sole insert 1234 of the sole member 1230 is brought into wedging engagement with the sole receiver 1224 of the base 1220. The proximal surface 1232 of the sole member 1230 is then rotated towards the base member 1220 until the latch member 1236 is lockingly received within the housing 1226 in a manner as discussed above with regards to numerous other embodiments. In this manner, the sole 1230 may be connected to the base portion 1220.

To remove the sole 1230 from the base portion 1220, the process is reversed. The latch member 1236 is removed from the housing 1226 and the proximal surface 1232 of the sole is rotated away from the base 1220 until the sole insert 1234 may be released from engagement with the sole receiver 1224. Thus, the plantar aspect of the foot is exposed for evaluation and treatment.

Of course suitable retaining and locking mechanisms may be provided on the off-loading walker and the sole assembly 1220 so that the patient may not remove either the walker or the sole member 1230 without a practitioner being present.

It will be recognized of course that the sole receiver or lip 1224 may be provided in the posterior portion of the base 1220, and the housing or latch receiving portion 1226 may be provided on the exterior, anterior portion of the base 1220. Further, the sole insert 1234 may be provided in a posterior portion of the sole member 1230 and the latch member 1236 may be provided in an anterior portion of the sole member 1230. An additional insole or cushion member may also be inserted through the opening 1222 prior to attaching the sole member 1230 to the base portion 1220 in order to form the contact surface for the plantar surface of the foot.

Another embodiment of a sole assembly for use with diabetic walkers is discussed next.

Figure 13:
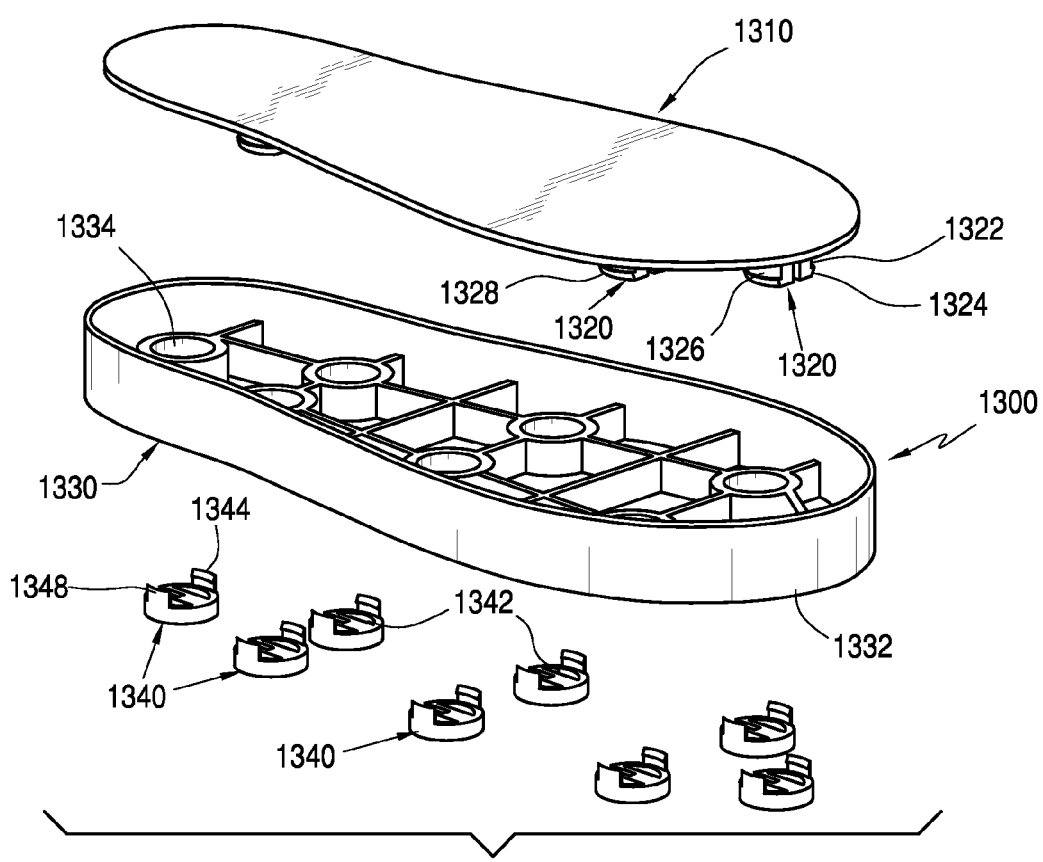
FIG. 13 is a perspective view of another embodiment of a sole assembly for an orthopedic device.

L. Detailed Description of Another Embodiment of a Sole Assembly for use with an ITCC with Easy Access to Wound Site FIG. 13 illustrates another embodiment of a sole assembly 1300 that may be used with an open ended orthopedic device such as a diabetic walker, in particular with any of the above or below described embodiments.

The sole assembly 1300 includes an upper sole member 1310 and a rocker sole member 1330 that are selectively connectable with each other in order to form a sole for a walker. As with other described embodiments, the upper sole member 1310 and the lower sole member 1330 may be formed from substantially rigid and resilient materials.

The upper sole member 1310 has at least one tab 1320 that is formed from first and second projections 1322, 1326 that extend distally from the distal surface of the upper sole member 1310. The first and second projections 1322, 1326 are spaced slightly apart so that the first and second projections 1322, 1326 may be bent towards each other for reasons that will be discussed in more detail below. Each of the first and second projections 1322, 1326 have snap portions 1324, 1328 formed around a distal periphery of the first and second projections 1322, 1326.

The rocker sole 1330 is defined by an outer peripheral wall extending proximally from a distal surface 1332 of the rocker sole 1330. Thus, an interior space is formed between the outer peripheral wall and the distal surface 1332 of the rocker sole 1330. A structural framework or box sections may be provided within the interior space in order to provide structural integrity to the rocker sole 1330. Passages 1334 are also defined in the interior space and passing through the distal surface 1332 of the rocker sole 1330 so that the interior space may be in communication, through the passages 1334, to the exterior surroundings of the rocker sole 1330.

In order to attach the sole assembly 1300 to a walker or other orthopedic device the upper sole member 1310 is wedged into the opening provided in the distal end of the walker or other orthopedic device. Thus the proximal surface of the upper sole defines the contact surface for the plantar surface of the foot. Of course, an insole or cushion may first be provided within the opening prior to wedging the upper sole member 1310 within the opening. In this case, the insole or cushion defines the contact surface for the plantar surface of the foot.

The rocker sole 1330 is next aligned with the upper sole member 1310 such that the tabs 1320 are aligned with the passages 1334 in the rocker sole member 1330. When the tabs 1320 and passages 1334 are aligned, the rocker sole 1330 may be moved in the proximal direction towards the upper sole 1310 so that the tabs 1320 are received in the passages 1334. The cross-sectional size of the tabs 1320 may be slightly larger than the cross-sectional size of the passages 1334, such that the first and second projections 1322, 1326 of the tabs 1320 are bent towards each other. Alternatively, the cross-sectional size of the tabs 1320 may be such that they have a friction-fit or a clearance fit with the cross-sectional size of the passages 1334.

In either case, additional locking structures in the form of latches or pegs 1340 are provided to engage the tabs 1320 in order to selectively lock the rocker sole 1330 to the upper sole member 1310. The pegs 1340 have the same cross-sectional shape as the passages 1334 and the tabs 1320. The pegs 1340 are defined by a base portion from which first and second snap projections 1344, 1348 extend in the proximal direction.

Once the rocker sole 1330 is in engagement with the upper sole member 1310, the pegs 1340 are inserted into the passages 1334 so that the first and second snap projections 1344, 1348 respectively engage and lock with the snap portions 1324, 1328 of the tabs 1320. The resiliency of the first and second projections 1322, 1326 of the tabs 1320 acts to expand the first and second snap projections 1344, 1348 of the pegs 1340 such that the first and second snap projections 1344, 1348 press against the inner surfaces of the passages 1334. In this manner, the rocker sole 1330 is locked onto the upper sole 1310.

The rocker sole 1330 may be removed from the upper sole 1310 in the following manner. Slots 1342 are provided in the base of the pegs 1340. A thin object, such as the flat edge of a screwdriver, may be inserted into the slots 1342 in order to act as a pry bar or lever for prying the pegs 1340 from within the passages 1334. The rocker sole 1330 may be easily pulled distally away from the upper sole 1310 once all of the pegs 1340 have been removed. Then the upper sole 1310 may be pulled distally from the opening in the walker by utilizing the tabs 1320 for gripping mechanisms. Thus, the plantar surface of the foot may be uncovered for examination and treatment of plantar ulcerations.

It will be recognized that the size, shape, and number of passages, tabs, and pegs may be varied based upon numerous factors, for example the weight of the patient. Additionally, replacement pegs may be provided to physicians and practitioners in case of breakage of the originally provided pegs.

An additional embodiment of an orthopedic device in the form of a low top or walker boot is discussed next.

M. Detailed Description of a Removable Sole Orthopedic Device

Figure 14A:
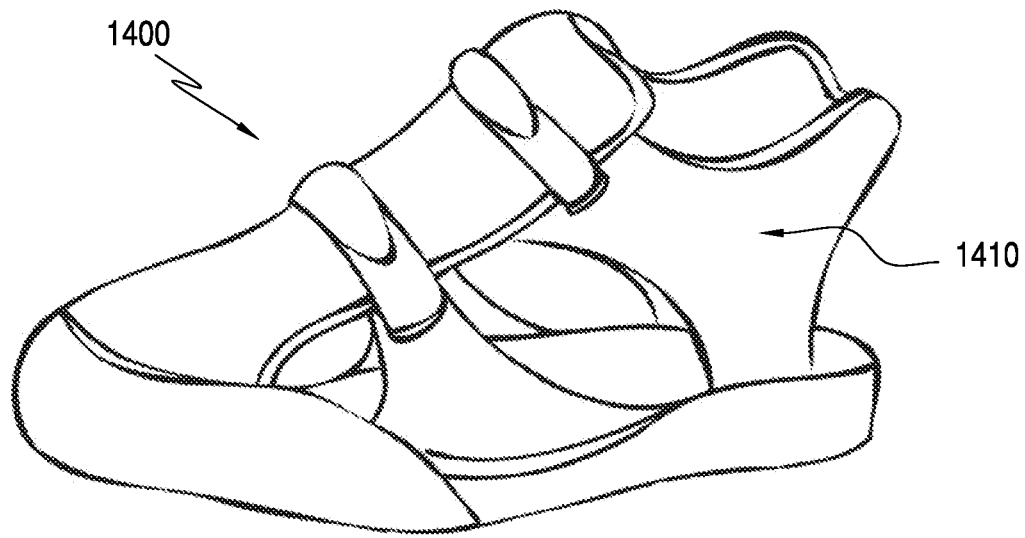
FIG. 14A is a perspective view of another embodiment of an orthopedic device.
Figure 14B:
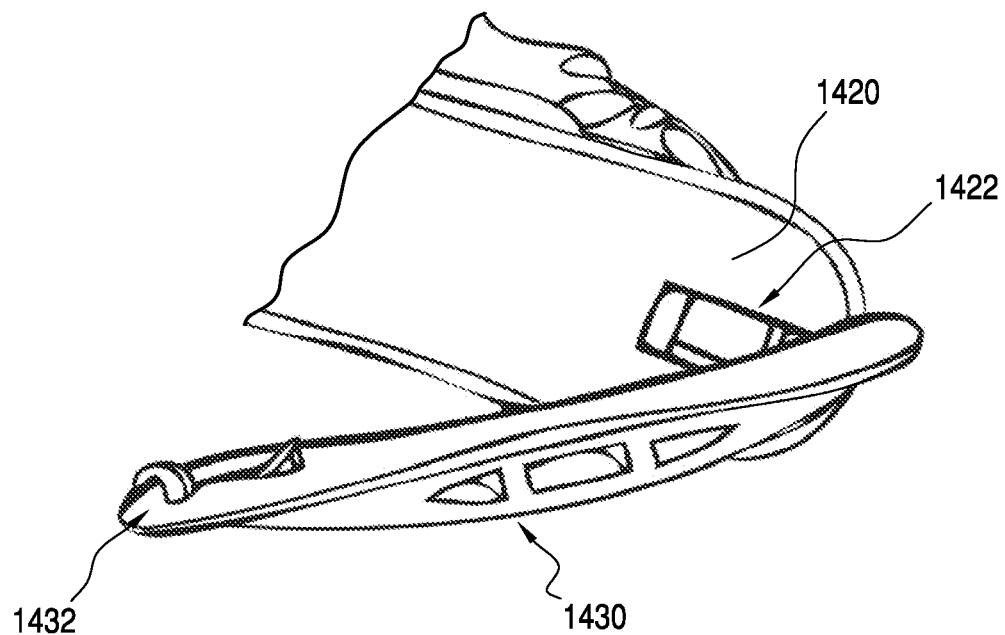
FIG. 14B is a partial perspective view of the sole of the orthopedic device in FIG. 14A.

An embodiment of a low top or walker boot 1400 having a removable sole is shown in FIGS. 14A and 14B. The low top or walker boot 1400 includes an upper body portion 1410. A base portion having a distal surface 1420 is provided along the distal portion of the body 1410. A clip member slot 1422 having appropriate engaging portions therein is provided in an anterior portion of the distal surface 1420. The engaging portions may be located in anterior and posterior portions of the clip slot 1422 and may be in the form of recessed portions, or rods or bars spanning the width of the clip member slot 1422.

A rocker sole member 1430 is provided having a clip member 1432 positioned in the anterior portion of the proximal surface of the rocker sole 1430. The clip member 1432 has a substantially rigid hook shaped portion in the anterior portion of the clip member 1432 for engaging the anterior engaging portion within the clip slot 1422. The clip member further includes a resilient flared portion in the posterior portion of the clip member 1432 for selectively engaging the posterior engaging portion of the clip slot 1422.

The rocker sole 1430 is attached to the body 1410 by first aligning the clip member 1432 of the sole 1430 with the clip slot 1422 on the distal surface 1420 of the body 1410. Once aligned, the anterior portion of the clip member 1432 is inserted into the clip slot 1422. The rocker sole 1430 may then be moved in the proximal direction towards the body until the posterior portion of the clip member 1432 also engages the posterior engaging portion in order to maintain the sole 1432 in position on the body 1410. The user will feel and/or hear a click when the clip member 1432 is properly engaged in the clip slot 1422.

To remove the rocker sole 1430 from the body 1410, the user simply pulls the sole 1430 firmly in the distal direction and then simultaneously pushes the sole in the distal and anterior directions until the clip member 1432 becomes completely disengaged from the clip slot 1422.

In this manner the rocker sole 1430 may be removed to allow inspection and treatment of the plantar surface of the patient's foot. Of course, suitable retaining and locking mechanisms may be provided in order to lock the body 1410 to the patient's leg and to lock the sole 1430 to the body 1410 so that the patient may not remove the walker boot 1400 or the sole 1430 from the body 1410 without the presence of the physician or practitioner.

It will be recognized that the removable sole of this embodiment may be utilized with any of the disclosed embodiments of a diabetic walker. It will further be recognized that the removable sole of this embodiment may be utilized with any other suitable form of diabetic footwear, such as diabetic shoes, in order to provide visual inspection of the plantar surface of the foot.

Another variation of a diabetic walker having a hinged sole is described next.

N. Detailed Description of a Variation of a Diabetic Walker Having a Hinged Sole As shown in FIG. 15, a variation of a diabetic walker 1500 having a hinged sole 1530 is provided. Similar to the embodiments of FIGS. 2A and 2B, the diabetic walker 1500 includes at least one strut 1510 that is connected to or integrally formed with the base 1520.

Similar to previous embodiments, slots or D-ring attachment points 1570, 1580 may be located on the base 1520, or the struts 1510 for providing anchors or attachment points for straps and/or buckles in a manner that will be recognized by a skilled artisan.

Also similar to previous embodiments, the proximal surface of the sole 1530 may define the contact surface for the plantar aspect of the foot. Alternatively, an insole or cushion member (not shown, see FIGS. 2A and 2B) may be positioned along the proximal surface of the sole 1530.

Also provided is a hinge mechanism 1540 that allows the sole 1530 to be rotated from the base 1520 in order to allow access and inspection of the plantar surface of a patient's foot. The hinge is formed in components that are positioned along at least one of the lateral and medial sides of the base 1520 and sole 1530.

Specifically, a guide groove 1522 is formed in at least one of the lateral and medial portions of the base 1520. A corresponding projection 1532 is positioned along the respective lateral and/or medial side of the sole 1530. The projection 1532 extends from the proximal surface or edge of the sole 1530 towards the base 1520. The projection is generally oriented in alignment with the guide groove 1522. A guide pin 1534 is positioned on a proximal end of the projection 1532 for engagement and guiding within the guide groove 1522.

In order to gain access to the plantar surface of the foot without removing the walker 1500 from the patient's leg, the sole 1530 is simply rotated away from the base 1520. The rotation is aided by the guide pin 1534 sliding within the guide groove 1522. The sole 1530 is rotated towards the base 1520 in order to prevent access to the plantar surface of the foot. Again, the rotation is aided by the guide pin 1534 sliding within the guide groove 1522.

Additionally, a hinge of the types shown in FIGS. 2A and 2B may also be provided along the posterior portions of the base 1520 and sole 1530. Such a hinge would further limit the motion of the sole 1530 with respect to the base 1520 to be within a predetermined plane.

Suitable locking mechanisms may be provided, such as any of the previously described locking mechanisms, in order to maintain the sole 1530 in position on the base 1520. Additionally, locking mechanisms to prevent the sliding of the guide pin 1534 within the guide groove 1522 may be provided, as will be recognized by a skilled artisan.

The hinge 1540 of this embodiment provides a structure to aid the physician with accessing the plantar surface of the patient's foot in a safe and convenient manner. The hinge 1540 specifically provides a well defined path of rotation of the sole 1530, such that there is reduced risk of unexpected contact between the sole 1530 and the plantar surface of the foot. Accordingly, there is a reduced risk of further damage to the plantar surface of the foot due to the movement of the sole 1530.

An embodiment of a diabetic walker utilizing a pivot or rotation point for a pivotable base and sole is described next.

O. Detailed Description of an Embodiment of a Diabetic Walker Having a Pivotable Sole As shown in FIG. 16, a variation of a diabetic walker 1600 having a pivotable base 1620 and sole 1630 is provided.

In the embodiment according to FIG. 16, the base 1620 and sole 1630 may be integrally formed or otherwise connected to each other, for example by rivets or adhesives. Thus, as with other embodiments, the base portion 1620 extends from the proximal surface of the sole 1630, at least along lateral and medial sides of the sole 1630.

Unlike previous embodiments, a pivot 1640 is positioned between the lateral and medial base portions 1620 and the struts 1610 in order to provide a pivoting motion between the base 1620 and the struts 1610. Accordingly, lateral and medial pivots 1640 are provided. Each pivot 1640 includes a distal leg 1642 that is attached to the base 1640 via rivets, adhesives, or any other suitable manner.

Each pivot also includes a proximal leg 1644 that is attached to a respective strut 1610 via rivets, adhesives, or any other suitable manner. The legs 1642, 1644 of the pivot 1640 are pivotally engaged with each other via a pin, rivet, or similar pivot point.

Thus, the base 1620 and the sole 1630 are able to be selectively pivoted, via the pivot 1640, with respect to the struts 1610. In this manner, the plantar surface of the foot may be exposed for access and inspection, while the struts 1610 remain in place on the user's limb. Appropriate indicia, such as lettering with arrows, instructing the physician on which direction to pivot the base 1620 and sole 1630 in order to "open" or "close" the diabetic walker 1600 is provided on the pivot 1640.

Similar to previous embodiments, slots or D-ring attachment points 1670, 1680 may be located on the base 1620, or the struts 1610 for providing anchors or attachment points for straps and/or buckles in a manner that will be recognized by a skilled artisan.

Also similar to previous embodiments, the proximal surface of the sole 1630 may define the contact surface for the plantar aspect of the foot. Alternatively, an insole or cushion member (not shown, see FIGS. 2A and 2B) may be positioned along the proximal surface of the sole 1630.

Suitable locking mechanisms may be provided, such as pivot pin locks for restricting the movement of the legs 1642, 1644 of the pivot 1640, may be provided in order to prevent the unauthorized access of the plantar surface of the foot. Other suitable locking mechanisms will be apparent to the skilled artisan.

The pivot 1640 of this embodiment provides a structure to aid the physician with accessing the plantar surface of the patient's foot in a safe and convenient manner. The pivot 1640 allows the entire sole 1630 and base 1620 to be pivoted away from the plantar surface of the foot and ankle without causing undue friction therebetween, thus limiting or preventing damage to the plantar surface of the foot. Additionally, since the base portion 1620 also pivots away from the ankle, a physician may also inspect the ankle of the patient for signs of injury or swelling.

An alternate configuration of the walker 1600 is shown in FIGS. 16A-C. As shown in FIG. 16A, the pivot 1640 includes a channel 1646 that receives a locking element 1648 therein. The locking element 1648 may be a locking screw, biased pin, or any other suitable locking element. In order to operate the pivot 1640, the locking element 1648 is loosened or unlocked so that the base 1620 and sole 1630 portions may be translated in the direction T away from the strut members 1610.

As can be seen in FIG. 16B, the locking element 1648 translates and is confined within the channel 1646 in order to define the outer limits of translation for the base 1620 and sole 1630 portions. As also shown in FIG. 16B, in the extended position, the sole 1630 does not contact the plantar surface of the foot.

Once the base 1620 and sole 1630 portions are in the extended position, the strut members 1610 may be rotated in the direction R such that the plantar surface of the foot and a portion of the ankle are exposed for inspection and treatment, without having to remove the walker 1600 from the patient's limb. In this manner, the sole 1630 does not contact the plantar surface of the foot during the rotation, and further damage or injury to the plantar surface of the foot is avoided.

The process is simply performed in reverse in order to place the walker 1600 into the operative configuration so that the patient may regain mobility.

P. Detailed Description of an Embodiment of a Diabetic Walker Having a Pivotable Base Portion Turning to FIGS. 17A and 17B, the upright and hinged configurations of the walker 1710 are depicted. As illustrated in FIG. 17A, the walker 1710 is in an upright configuration. This is exemplified by the locking mechanism 1720 having indicia 1722, in the preferred embodiment shown herein with an arrow, which indicates that the strut 1718 may be withdrawn from the side support 1716 so as to hinge the strut 1718 relative to the base 1714.

FIG. 17B depicts the struts 1718 pivoted about pivot point 1724 relative to the base 1714 via the hinging device 1732. In use, the hinging of the struts 1718 relative to the base 1714 permits inspection of the foot and ankle whereas the remainder of the walker is maintained on the leg via suitable strapping means by the struts 1718.

As illustrated in FIG. 17C, the locking device 1720 is rotatably mounted on the side support 1716. The locking device 1720 defines a resilient tip 1734 which is sized and configured for being retained within a recess 1736 formed on the strut 1718. In the event that it is desired to unlock the base 1714 from the strut 1718, one can lift up the resilient tip 1734 and turn the locking device 1720 so the resilient tip 1734 is no longer retained within the recess 1736.

Figure 17D:
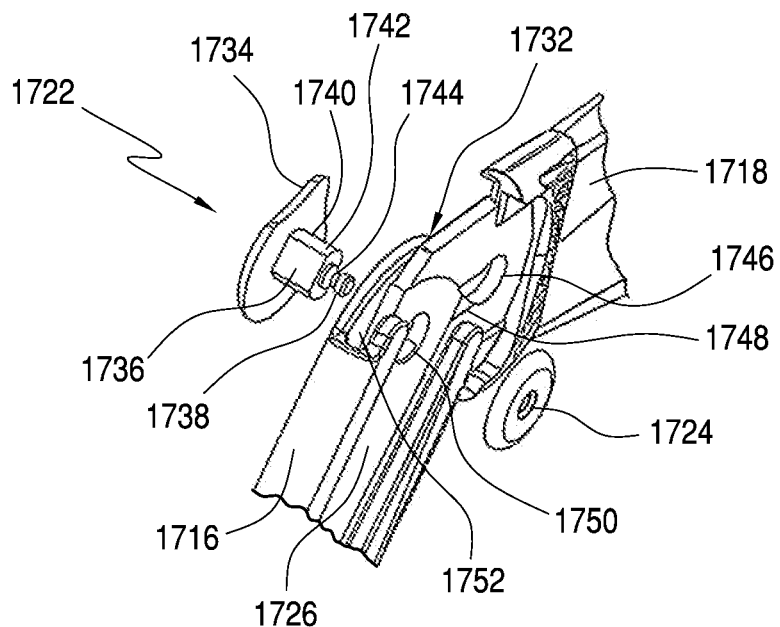
FIG. 17D is an exploded perspective view of a variation of a hinge device shown in FIG. 17B.

FIG. 17D depicts an embodiment of the hinge device 1732 and the locking device 1722, and their co-dependency. The strut 1718 preferably includes a hinge fitting located at a lower end thereof. According to one variation, the hinge fitting forms part of the hinge device 1732, and defines a main slot 1748 having the opposed enlarged portions 1746, 1747 located at opposed ends thereof through which a block 1740 formed on the face of a dial 1734 extends.

Figure 17E:
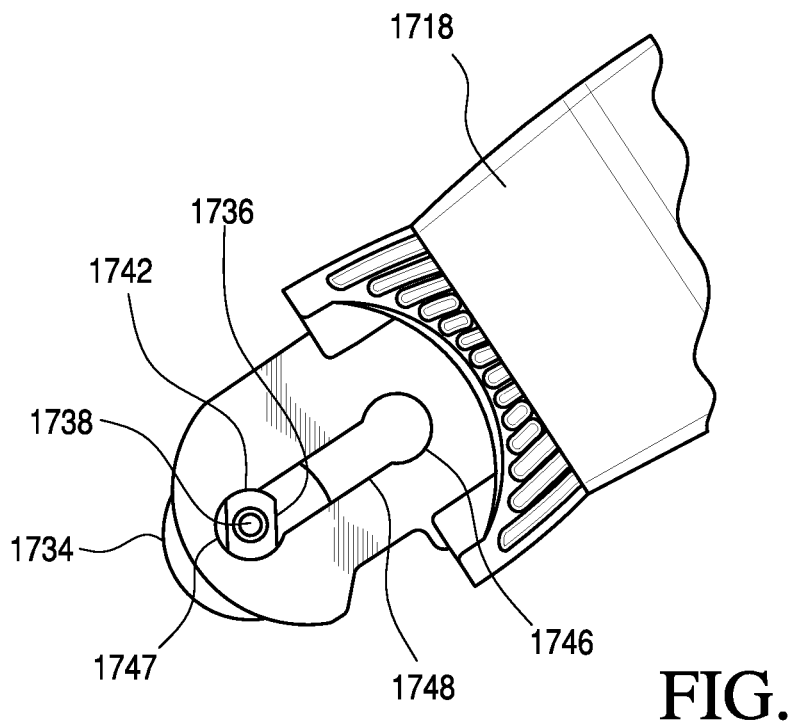
FIG. 17E is an elevational view of a partially assembled hinge device of FIG. 17D.

As shown in FIG. 17E, the block 1740 defines a protrusion having opposed arcuate sections 1742 spaced by linear sections 1736. The arcuate sections 1742 are sized and configured to permit rotation about the enlarged portions 1746, 1747, whereas the linear sections 1736, when aligned with the slot 1748, permit sliding of the block 1740 from enlarged portion 1746 to enlarged portion 1747, and vice versa.

The block 1740 further defines a pin 1738 with undercut notches 1744 located therebelow. The pin 1738 is adapted to extend through the slot 1748 extending from the hinge fitting and an aperture 1750 formed through the side support 1716, and according to some variations a frame or reinforcement member 1726. The pin 1738 is maintained through the hinge fitting 1754 and the side support 1716 via a cap 1724 having sections that engage the undercut notches 1744. The side support 1716 defines a niche 1752 which permits rotation and withdrawal of the strut 1718 from the side support 1716.

Various retaining mechanisms suitable for use with the diabetic walkers of this disclosure are discussed next.

Q. Detailed Description of Embodiments of Retaining Mechanisms for use with Diabetic Walkers As previously discussed, the orthopedic devices, diabetic walkers and orthopedic footwear of this disclosure may be locked or retained in place on the patient's limb or anatomical portion in order to ensure proper patient compliance. Suitable methods discussed above include the use of casting tape and various strapping mechanisms. A number of additional retaining mechanisms are discussed below that aid in maintaining the orthopedic devices, diabetic walkers and orthopedic footwear in place on the patient's limb.

Figure 18:
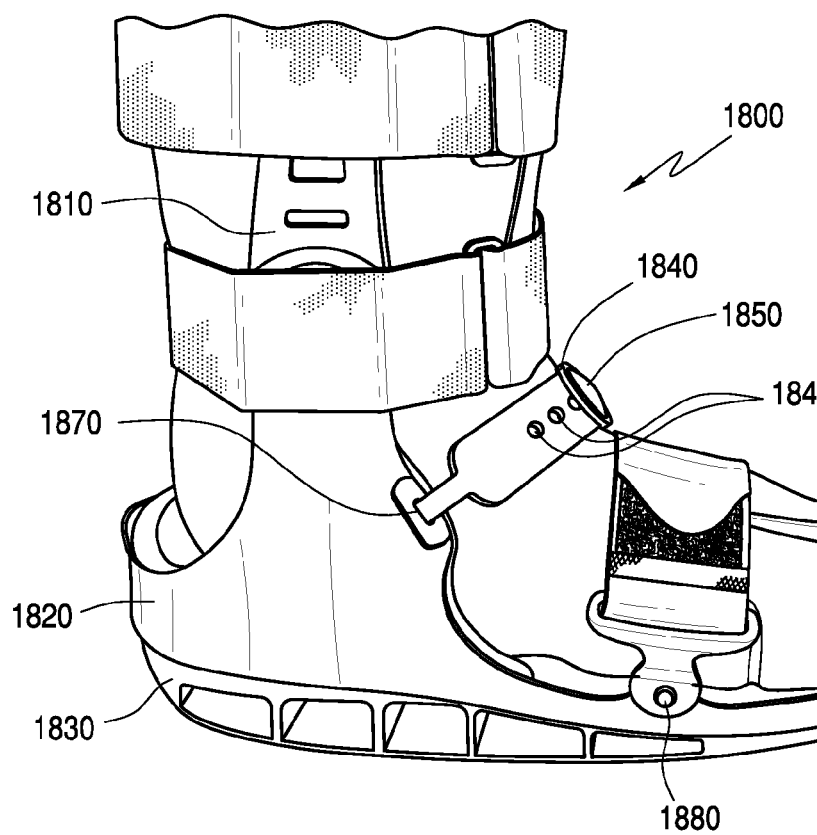
FIGS. 18-25 are perspective side views of alternative variations of a retaining strap for use with an orthopedic device.

A first exemplary retaining strap is shown in FIG. 18 in use on a walker 1800 having a sole 1830, base 1820, and struts 1810. As can be seen, D-rings are attached at the attachment point 1880, corresponding to the D-ring attachment points of previously discussed embodiments.

The retaining strap 1840 may have first and second portions that engage the walker 1800 at respective lateral and medial sides of the base 1820 at the slots 1870, corresponding to previously discussed slots, and is used for tightening and retaining the walker 1800 on the patient's limb.

Each of the portions of the retaining strap 1840 defines holes 1842. To tighten the retaining strap 1800, the holes 1842 from each portion are aligned and a retaining knob 1850, which includes a snap projection, is snap fit within the holes 1842 in order to lock the retaining strap 1840 in position. The retaining knob 1850 is removed in order to loosen the retaining strap 1840.

Figure 19:
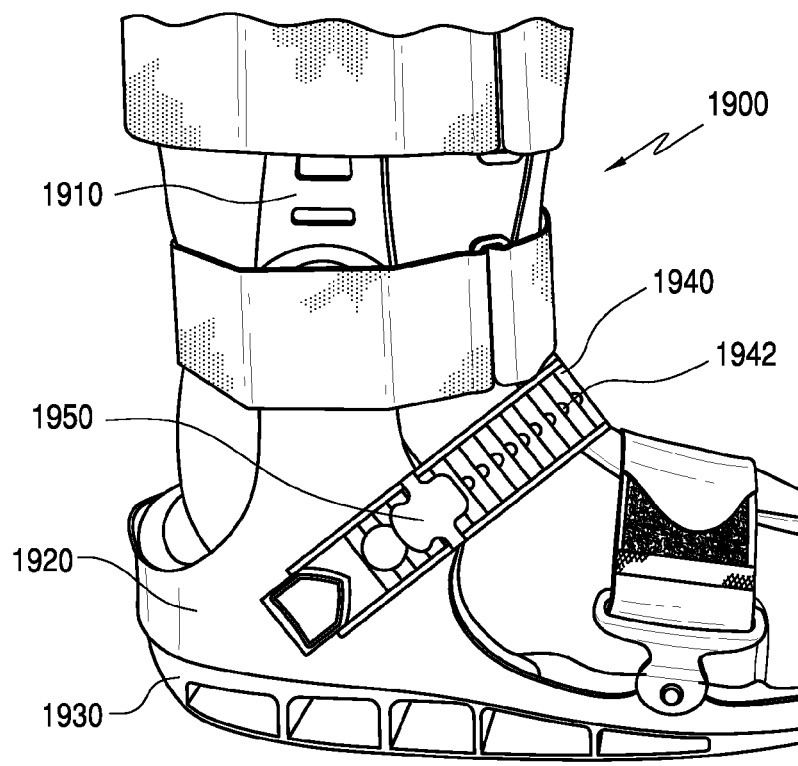

An alternative retaining strap 1940 is shown in FIG. 19 in use on a walker 1900 having a sole 1930, base 1920, and struts 1910. This retaining strap is a ladder bracket having a lever 1950 pivotably secured to the base 1920 and engages one of numerous grooves and holes 1942 of the retaining strap 1940. The grooves and holes 1942 may be provided with indicia that correlate to a degree of tensioning of the strap 20 against the dorsum.

Preferably, the lever 1950 is biased towards the strap 1940. A first end of the lever 1950 engages one of the grooves and holes 1942 of the strap 1950 and secures the strap 1950 from movement relative to the base 1920. Of course, if pressed at a second end opposite the first end, the lever 1950 is released from one of the grooves and holes 1942 and the strap 1940 may be adjusted relative to the lever 1950 accordingly. Exemplary straps of this type are described in more detail in U.S. Pat. No. 7,198,610, granted Apr. 3, 2007, commonly owned by Össur hf, and herein incorporated by reference.

Figure 20:
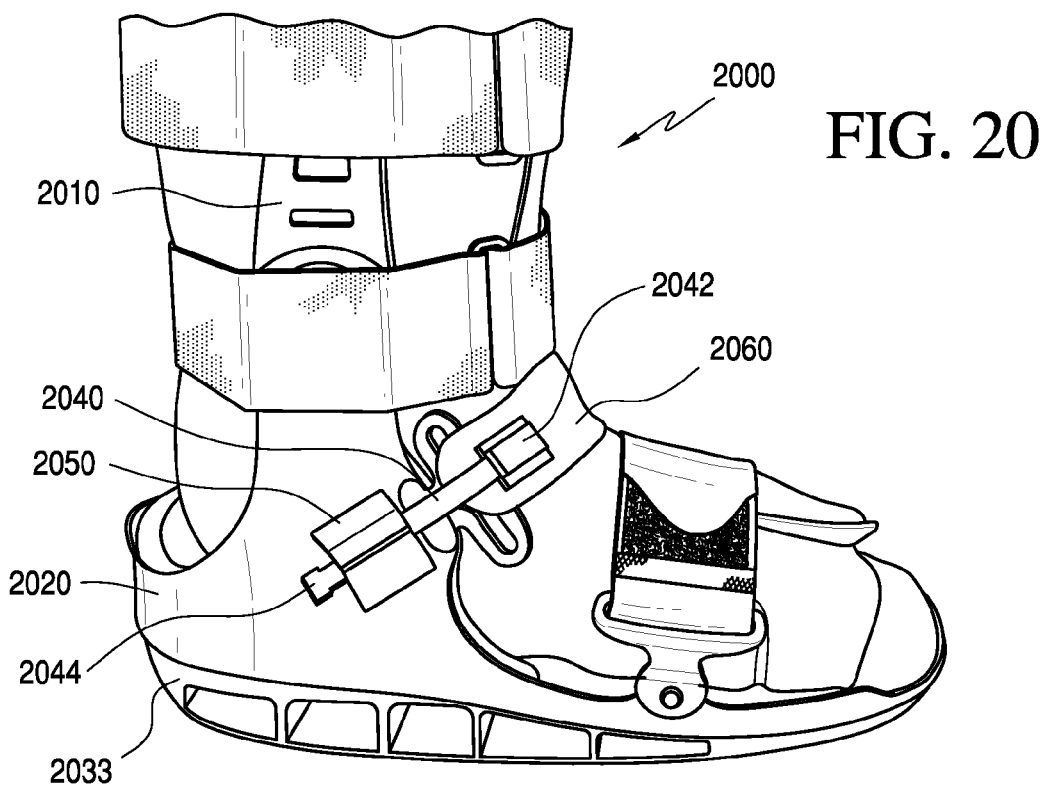

In another embodiment, a retaining strap 2040 is shown in FIG. 20 in use on a walker 2000 having struts 2010, a base 2020, and a sole 2030. The retaining strap 2040 may be a length of plastic having first 2042 and second 2044 ends. The first end 2042 may be secured in any suitable manner to a broad strap 2060, which is made of typical strap material. The second end 2044 may be selectively engaged with a retaining plug 2050 that is secured to or integrally formed with the base 2020.

The retaining plug 2050 may have internal ratchet or pawls that engage a corresponding pawl or ratchet on the retaining strap 2040 in order to provide tightening of the retaining strap 2040 in a known manner. Any excess material of the retaining strap 2040 at the second end 2044 may be trimmed.

Figure 21:
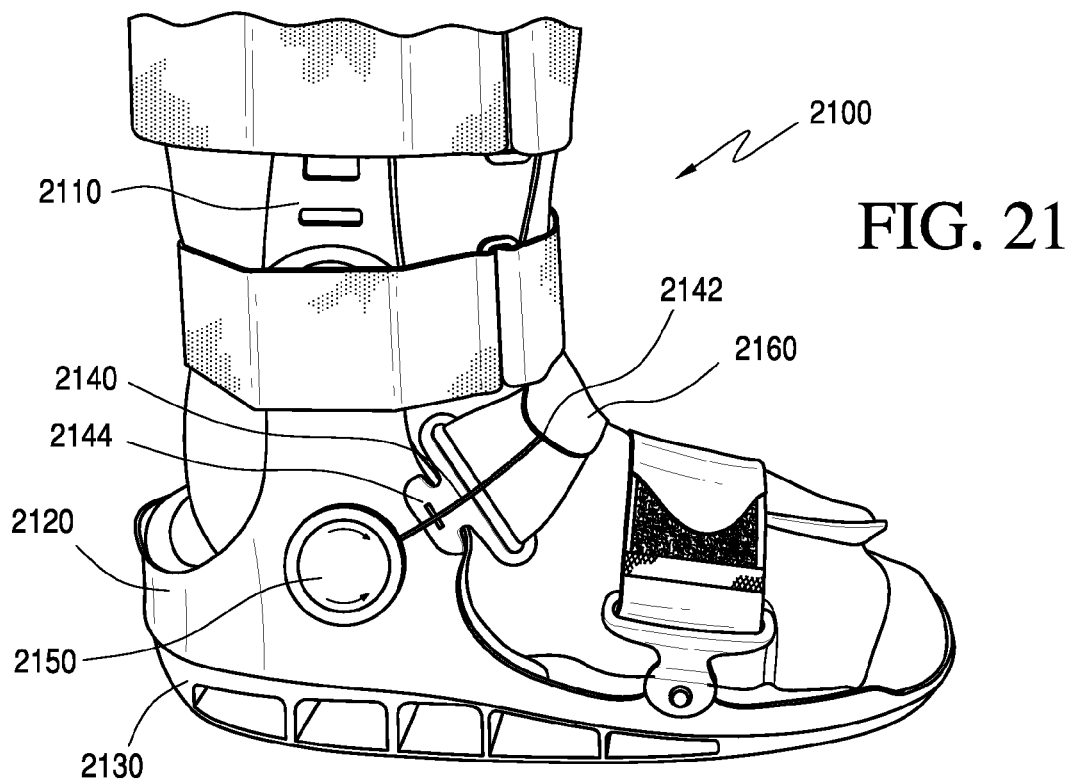

In another embodiment, a retaining cable/strap 2140 is shown in FIG. 21 in use on a walker 2100 having struts 2110, a base 2120, and a sole 2130. This retaining cable/strap 2140 may have a first end 2142 secured to a wide strap 2160 in any suitable manner and a second end that is engaged with a tightening knob 2150. Rotation of the knob in one direction may tighten the strap 2140 and rotation in the other direction may loosen the strap 2140. A commercial example of such a tightening device includes BOA lacing system of BOA Technology Inc. of Steamboat Springs, Colo., as described in U.S. Pat. No. 6,289,558, granted Sep. 18, 2001, and herein incorporated by reference.

Figure 22:
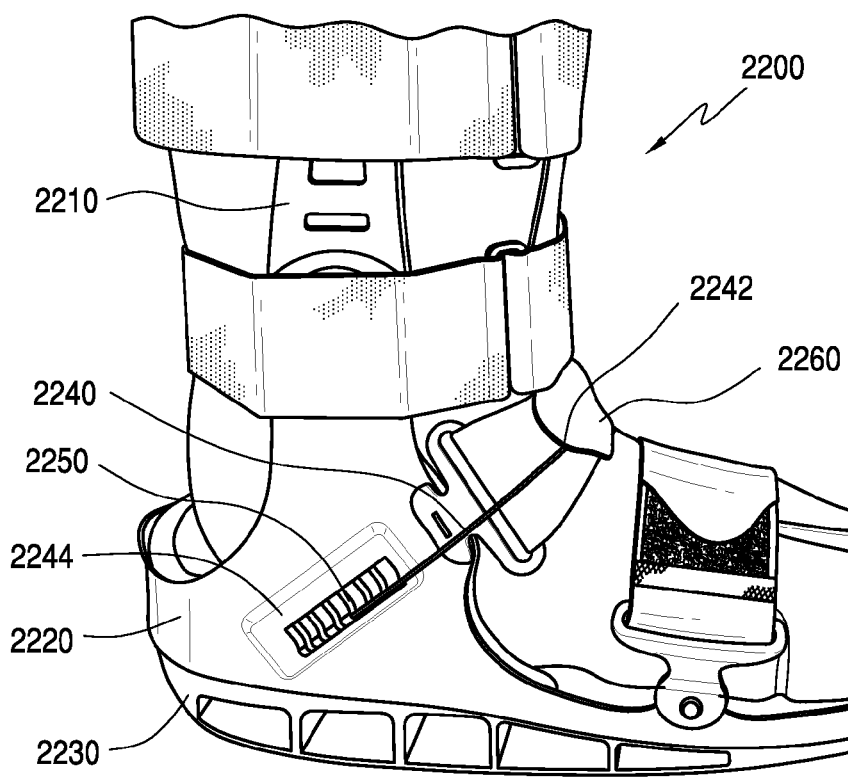

A similar embodiment of a retaining cable/strap 2240 is shown in FIG. 22 in use on a walker 2200 having struts 2210, a base 2220, and a sole 2230. The retaining cable/strap 2240 may have a first end 2242 secured to a broad strap 2260 in any suitable manner and a second end 2244. The second end 2244 may include an enlarged or flared portion, knob, plug, or bead. The second end 2244 may be received and retained in a selective one of a number of retaining recesses in the retaining housing 2250, which may be secured to or integrally formed with the base 2220.

The retaining recesses have an enlarged portion that allows the bead or plug of the second end 2244 to pass therethrough. The retaining recesses also have a reduced size portion that allows the cable 2240 to pass therethrough, but prevents the passage of the bead or plug of the second end 2244. In this manner, the retaining cable/strap 2240 may be selectively tightened or loosened and locked in position.

Figure 23:
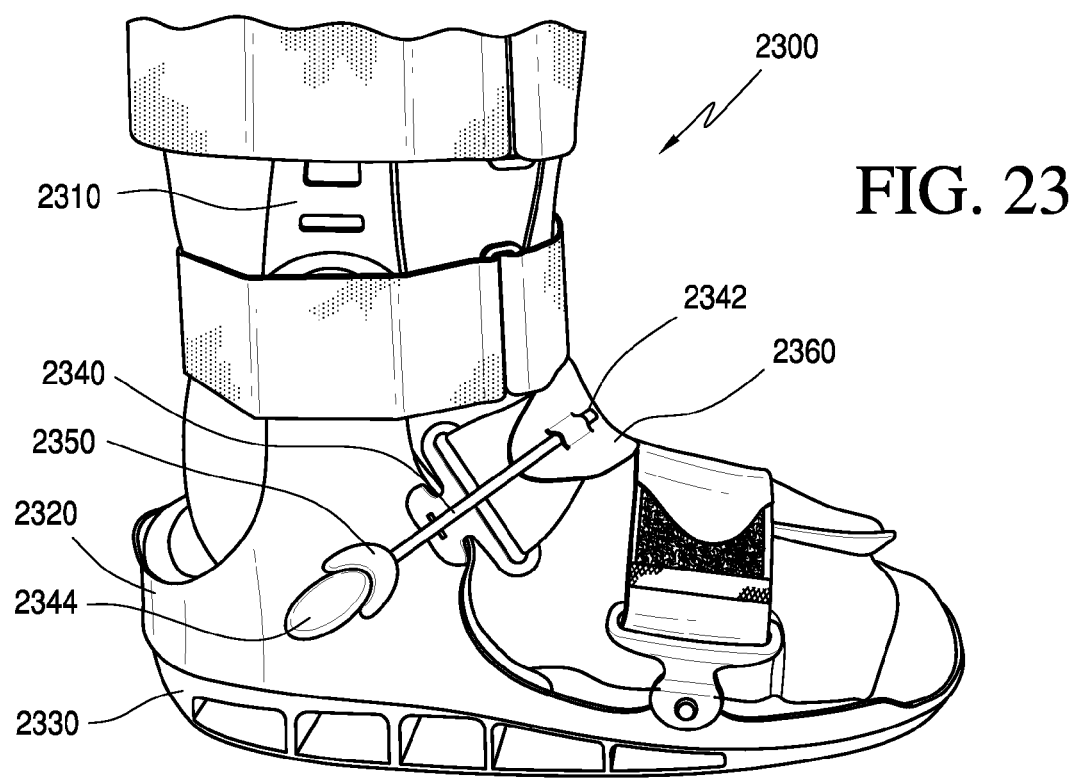
Figure 24:
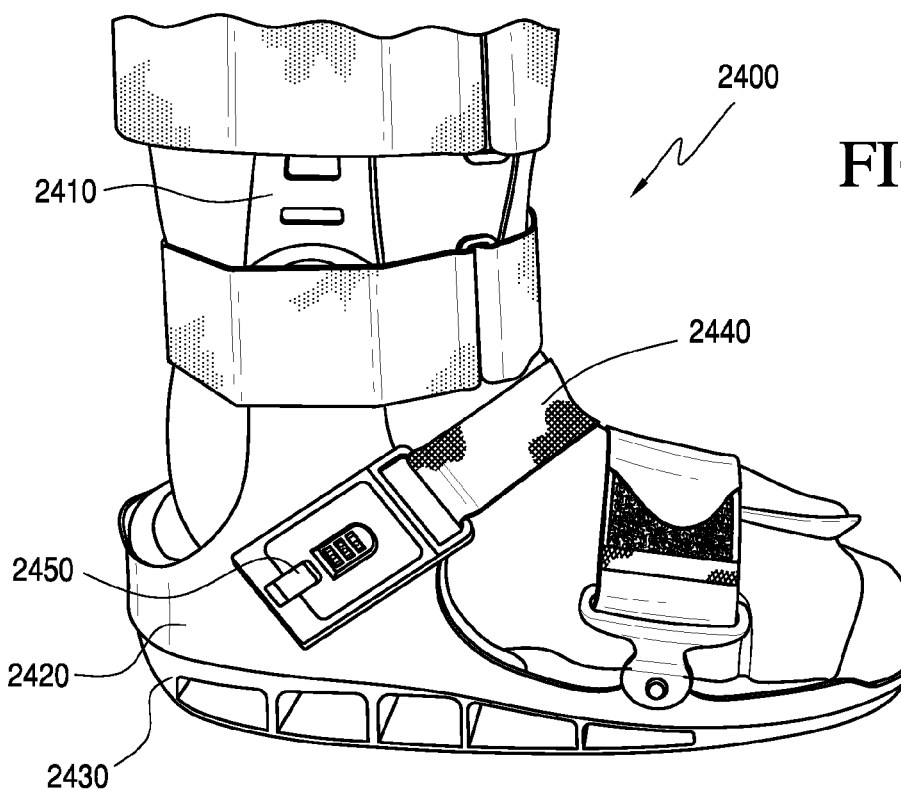

A further alternative retaining strap 2340 is shown in FIG. 23 in use on a walker 2300 having struts 2310, a base 2320, and a sole 2330. The retaining strap 2340 is in the form of a plastic cable having a first end 2342 threaded through passages in a broad strap 2360. The second end 2344 of the retaining strap 2340 has an enlarged portion that engages the retaining plug 2350, which is selectively engagable with the base 2320.

A similar arrangement may be provided on the opposed side of the walker 2300 that is hidden from view. Different lengths of a retaining strap 2340 having the same configuration may be provided in order to adjust the tightness of the retaining strap 2340.

In yet another embodiment, a retaining strap 2440 is shown in use on a walker 2400 having struts 2410, a base 2420, and a sole 2430. The retaining strap 2440 may be secured to a retaining lock 2450. The retaining lock 2450 may be provided with a combination lock, or a key lock, in a known manner, in order to prevent any unauthorized removal or adjustment of the retaining strap 2440.

Figure 25:
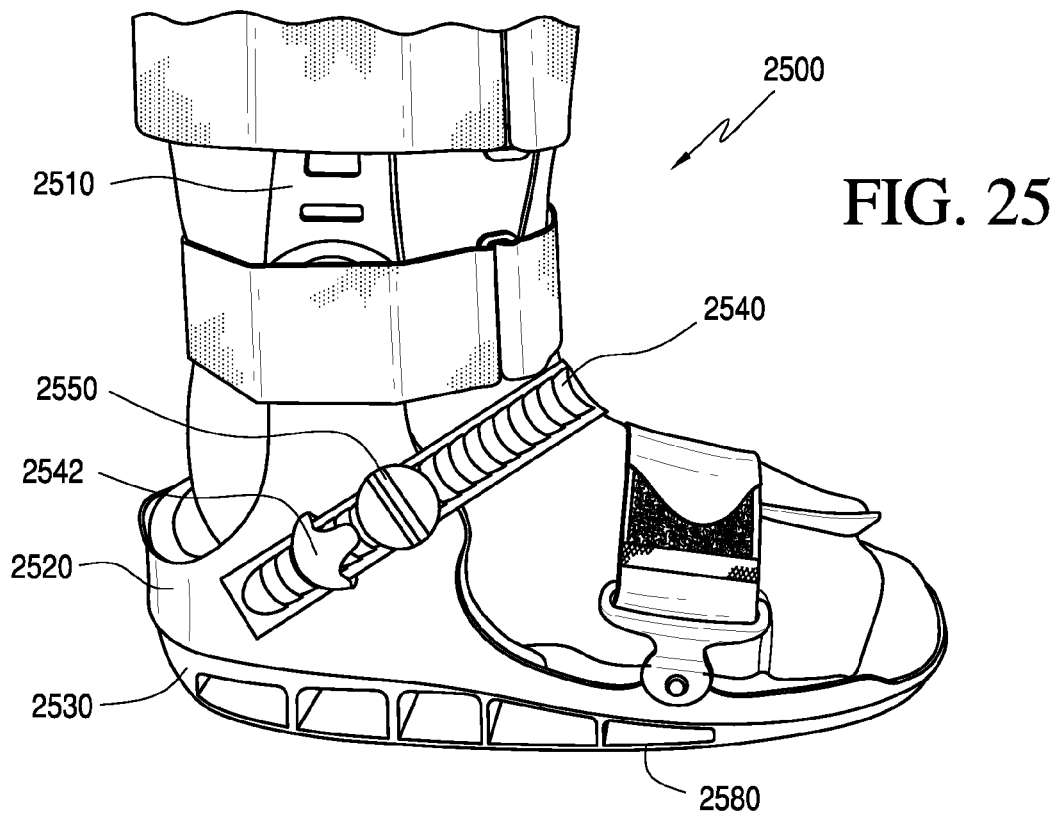

In yet another embodiment, an exemplary retaining strap is shown in FIG. 25 in use on a walker 2500 having a sole 2530, base 2520, and struts 2510. As can be seen, D-rings are attached at the attachment point 2580, corresponding to the D-ring attachment points of previously discussed embodiments.

The retaining strap 2540 engages the walker 2500 at both ends of the strap and is used for tightening and retaining the walker 2500 on the patient's limb. To tighten the retaining strap 2500, the loose end of the strap is fed through the rotatable retaining knob 2550, which is fixed to the walker 2500 at the slot identified in numerous embodiments.

The retaining strap 2540 includes a number of raised portions or stops 2542 that extend across the width of the strap 2540. The strap 2540 is tightened and these stops 2542 are engaged by the retaining knob 2550 when the retaining knob 550 is rotated to a first position in order to lock the retaining strap in place. To release the strap 2540, the knob 2550 is rotated to a second position such that the stops 2542 are not engaged and that allows the strap 2540 to be tightened or loosened. A bracket may be provided to retain the loose end of the retaining strap 2540.

Of course, it will be recognized that any of the retaining straps disclosed herein may be utilized with any of the embodiments of diabetic footwear disclosed herein. Further, it will be recognized that various features of the retaining straps may be modified with features from any other embodiment of a retaining strap. It will also be apparent to a skilled artisan that different variations of the retaining strap may be utilized with a single orthopedic device in order to allow for changes in the patient compliance, such that throughout the treatment period, if a patient shows improved or less compliance, the retaining strap may be interchanged and replaced accordingly.

It will also be recognized that varying degrees of preventative adjustment and removal may be utilized, depending on the amount of patient compliance. All of the retaining straps disclosed herein are designed to improve patient compliance by increasing the level of dexterity and the amount of difficulty required to remove or adjust the retaining straps. This is in contrast to the typical simple hook and loop fasteners which require very little dexterity to remove or adjust. In this manner, the diabetic footwear of the present disclosure aids with patient compliance in utilizing the diabetic footwear as directed by the physician. Further, the diabetic footwear may be retained on the patient's limb by the retaining strap, in combination with standard straps, while the physician accesses, inspects, and treats the plantar surface of the foot.

R. Conclusion

The disclosed embodiments of an orthopedic device, orthopedic footwear or diabetic walker provide many improvements and allow easy access to a wound site on the plantar surface of the foot. In essence, it is the only way to have one product that can be left on the lower limb of the user generally but still allows for visual inspection of a wound site. Other advantages are, for example, easier and faster access to plantar ulcerations when conducting scheduled clinic, hospital, or home visits.

The disclosed embodiments allow removal of the base and/or sole of the diabetic walker only. Thus, there is no associated inconvenience of removing the entire off-loading walker during scheduled clinic, hospital, or home visits.

A further advantage is increased patient compliance of wearing the off-loading structure continuously, due to the non-removable aspect, as well as the improved comfort and reduced bulk of the product.

The structure of the disclosed embodiments also allows for the direct application of advanced dressings or pharmaceuticals that require frequent dressings changes to the wound site while still providing for a non-removable off-loading device.

Further, due the fact that appointment times or visit times can be reduced, and since casting materials do not need to be repeatedly removed, discarded and new casting materials applied, the disclosed embodiments provide a lower cost alternative to current TCCs and ITCCs. Further, the disclosed embodiments provide increased ease of use over current TCCs and ITCCs.

It is understood that the size of the disclosed embodiments and the components thereof can be adjusted so that different users having different sized legs, ankles, and feet may benefit from the present design. Specifically, the width, thickness and length of the struts and sole members may be varied to accommodate different sized users.

It is also understood that the embodiments disclosed may be assembled prior to applying the walkers to the patient's limb for the first time. Alternatively, portions of the walkers may be applied to the patient's limb and remaining portions may be subsequently attached to the portions maintained on the patient's limb. For example, strut and base members may be attached to the patient followed by connecting a removable sole to the strut and base portions. Alternatively, a sole member may be attached to the patient's limb and strut members may be subsequently attached to the sole member and then to the patient's limb.

It will also be recognized that the removable and/or movable sole aspects of the present disclosure are not limited to use with off-loading walkers, but are suitable for use with any type of orthopedic devices and footwear where it may be beneficial to provide access to the plantar surface of the foot or other portions of a wearer's anatomy.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. For example different locking mechanisms may be freely changed and substituted. Of course, suitable locking mechanisms to prevent the patient from exposing the plantar surface of the foot may be provided for each embodiment discussed above. In addition to the variations described herein, other known equivalents for each feature can be mixed and matched by one of ordinary skill in this art to construct an instant total contact cast with easy access to a wound site in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A leg mounted walker, comprising:
a sole member adapted to receive a foot of wearer;
a base member adapted to surround at least part of a foot and secure against an ankle of a wearer, the sole member is located at a bottom portion of the base member, the base member having at least one side support extending upwardly toward a top portion of the base member and defining an aperture extending therethrough and a niche defined at an uppermost portion of the at least one side support; and
at least one strut adapted to secure against a lower leg of a wearer, the at least one strut being movably mounted to the at least one side support and received by the niche and lockable in an upright position relative to the base by a locking device, the at least one strut defining an elongate main slot at an end portion thereof and enlarged portions spaced apart by and located at opposed ends of the main slot;
wherein the locking device includes a block extending through the main slot and the aperture of the side support to connect the at least one strut and the base member;

wherein the niche permits rotation and withdrawal of the strut from the side support.

2. The leg mounted walker according to claim 1, further comprising a retaining strap mounted on opposed sides of the base member, the retaining strap adapted to lock a foot of a wearer relative to the base member.

3. The leg mounted walker according to claim 2, wherein the retaining strap includes a series of incremental settings for securing the retaining strap to a foot of a wearer.

4. The leg mounted walker according to claim 1, wherein the sole member includes an upper sole member and a rocker sole member, the upper sole member being detachably secured to the rocker sole member.

5. The leg mounted walker according to claim 4, wherein a retaining and locking mechanism secures the upper sole member to the rocker sole member, the retaining and locking mechanism comprising at least a locking element extending from at least one of the upper sole member and the rocker sole member, and an opening formed by at least one of the upper sole member and the rocker sole member, the locking element arranged for being received by the opening to retain and lock the upper sole member to the rocker sole member.

6. The leg mounted walker according to claim 1, wherein the block defines a cross-section having opposed arcuate sections and opposed linear sections, the linear sections permitting sliding of the at least one strut along a single line.

7. The leg mounted walker according to claim 6, wherein a pin extends from a first end portion of the block and a cap secures to the pin and abuts against the base member.

8. The leg mounted walker according to claim 1, wherein the at least one strut includes a pair of struts and the at least one side support includes a pair of side supports, the pair of struts are detachably mounted to the pair of side supports.

9. The leg mounted walker according to claim 1, wherein the locking device includes a resilient tip sized and configured to be retained by a recess formed on the at least one strut.

10. A leg mounted walker, comprising:
a base member adapted to surround at least part of a foot and secure against an ankle of a wearer, the base member having a vertically upwardly extending side support defining a niche; and
a strut adapted to secure against a lower leg of a wearer and movably mounted to the side support, a first end portion of the strut being received by the niche, wherein the first end portion of the strut defines a main slot and enlarged portions spaced apart by and located at opposed ends of the main slot;
a locking device arranged to secure the strut to the side support in an upright position by extending through each of the strut and the side support, the locking device defining a block having a cross-section with arcuate sections opposed from one another spaced by linear sections, wherein the arcuate sections are sized and configured to permit rotation about the enlarged portions.

11. The leg mounted walker according to claim 10, wherein the main slot is arranged to receive the block so that the linear sections permit sliding of the at least one strut along a single line relative to the side support between the enlarged portions.

12. The leg mounted walker according to claim 11, wherein a pin extends from a first end portion of the block and a cap secures to the pin and abuts against the side support.

13. The leg mounted walker according to claim 10, wherein the locking device includes a resilient tip sized and configured to be retained by a recess formed on the at least one strut.

14. A leg mounted walker, comprising:
a base member adapted to surround at least part of a foot and secure against an ankle of a wearer, the base member having a vertically upwardly extending side support defining opposed sides spaced apart by a niche; and
a strut adapted to secure against a lower leg of a wearer and movably mounted to the side support, a first end portion of the strut being received by the niche, wherein the niche permits rotation and withdrawal of the strut from the side support;
a locking device arranged to secure the strut to the side support in an upright position by extending through each of the strut and the side support to engage the opposed sides of the side support;
wherein the first end portion of the strut defines a main slot having an elongate section and enlarged portions at opposed ends of the elongate section, the locking device defines a block having a cross-section with arcuate sections opposed from one another and linear sections opposed from one another, the main slot is arranged to receive the block so that the linear sections permit sliding of the at least one strut along a single line relative to the side support within the elongate section.

15. The leg mounted walker according to claim 14, wherein the locking device includes a resilient tip sized and configured to be retained by a recess formed on the at least one strut.

* * * * *